United States Patent
Shi et al.

(10) Patent No.: US 7,595,190 B2
(45) Date of Patent: Sep. 29, 2009

(54) TRANSPORTERS AND THEIR USES

(76) Inventors: Huazhong Shi, 5905 88th Pl., Lubbock, TX (US) 79424; Eduardo Blumwald, 612 Jerome St., Davis, CA (US) 95616

( * ) Notice: Subject to any disclaimer, the term of this patent is extended or adjusted under 35 U.S.C. 154(b) by 223 days.

(21) Appl. No.: 10/520,497

(22) PCT Filed: Jul. 9, 2003

(86) PCT No.: PCT/US03/21549

§ 371 (c)(1),
(2), (4) Date: Sep. 14, 2005

(87) PCT Pub. No.: WO2004/007668

PCT Pub. Date: Jan. 22, 2004

(65) Prior Publication Data

US 2006/0168697 A1    Jul. 27, 2006

Related U.S. Application Data

(60) Provisional application No. 60/395,662, filed on Jul. 12, 2002.

(51) Int. Cl.
*C12N 15/00* (2006.01)
*C07H 21/04* (2006.01)
*C07K 14/415* (2006.01)
*A01H 1/00* (2006.01)

(52) U.S. Cl. .................. 435/320.1; 435/6; 435/69.1; 435/466; 435/419; 530/370; 536/23.6; 800/278; 800/295

(58) Field of Classification Search ................ 536/23.1; 435/6, 468, 419, 320.1; 800/278, 295; 530/370
See application file for complete search history.

(56) References Cited

FOREIGN PATENT DOCUMENTS

CA    2 313 449 A1    1/2002
WO    WO 02/16423 A2    2/2002

OTHER PUBLICATIONS

Gaxiola et al., PNAS, vol. 96, No. 4, pp. 1480-1485, Feb. 1999.*
Apse, M., et al., "Salt Tolerance Conferred by Overexpression of a Vacuolar $Na^+/H^+$ Antiport in *Arabidopsis*" *Science*, Aug. 20, 1999, vol. 285, pp. 1256-1258.
Yokoi, S., et al., "Differential expression and function of *Arabidopsis thaliana* NHX $Na^+/H^+$ antiporters in the salt stress response," *The Plant Journal*, 2002, vol. 30, No. 5, pp. 529-539.
Zhang, H-X, et al., "Engineering salt-tolerant Brassica plants: Characterization of yield and seed oil quality in transgenic plants with increased vacuolar sodium accumulation," *PNAS*, Oct. 23, 2001, vol. 98, No. 22, pp. 12832-12836.
Chauhan, S. "Putative Na+/H+ Antiporter," EMBL Genbank Database Accession No. Q9LKH5, Oct. 21, 2000, 2 pages.
Waterstone, R. "A_TN021b04.4 Protein," EMBL Genbank Database Accession No. O04655, Jul. 1, 1997, 1 pages.
Waterstone, R. "Arabidopsis Thaliana BAC TM021B04," NCBI Genbank Database Accession No. AF007271, Jun. 6, 1997, 30 pages.

* cited by examiner

*Primary Examiner*—Phuong T Bui
(74) *Attorney, Agent, or Firm*—Townsend and Townsend and Crew LLP

(57) ABSTRACT

The present invention is generally related to plant genetic engineering. In particular, the invention is directed to nucleic acids and methods for conferring salt tolerance on plants and other organisms.

11 Claims, 6 Drawing Sheets

TRANSPORTERS AND THEIR USES

STATEMENT AS TO RIGHTS TO INVENTIONS MADE UNDER FEDERALLY SPONSORED RESEARCH OR DEVELOPMENT

This invention was made with Government support under Grant No. IBN 0110622, awarded by the National Science Foundation. The government has certain rights in this invention.

CROSS-REFERENCES TO RELATED APPLICATIONS

Not Applicable

FIELD OF THE INVENTION

The present invention is generally related to plant genetic engineering. In particular, the invention is directed to nucleic acids and methods for conferring salt tolerance on plants and other organisms.

BACKGROUND OF THE INVENTION

Environmental stress due to salinity is one of the most serious factors limiting the productivity of agricultural crops, which are predominantly sensitive to the presence of high concentrations of salts in the soil. Large terrestrial areas of the world are affected by levels of salt inimical to plant growth. It is estimated that 35-45% of the 279 million hectares of land under irrigation is presently affected by salinity. This is exclusive of the regions classified as arid and desert lands, (which comprise 25% of the total land of our planet). Salinity has been an important factor in human history and in the life spans of agricultural systems. Salt impinging on agricultural soils has created instability and has frequently destroyed ancient and recent agrarian societies. The Sumerian culture faded as a power in the ancient world due to salt accumulation in the valleys of the Euphrates and Tigris rivers. Large areas of the Indian subcontinent have been rendered unproductive through salt accumulation and poor irrigation practices. In this century, other areas, including vast regions of Australia, Europe, southwest USA, the Canadian prairies and others have seen considerable declines in crop productivity.

Although there is engineering technology available to combat this problem, through drainage and supply of high quality water, these measures are extremely costly. In most of the cases, due to the increased need for extensive agriculture, neither improved irrigation efficiency nor the installation of drainage systems is applicable. Moreover, in the arid and semi-arid regions of the world water evaporation exceeds precipitation. These soils are inherently high in salt and require vast amounts of irrigation to become productive. Since irrigation water contains dissolved salts and minerals, an application of water is also an application of salt that compounds the salinity problem.

Increasing emphasis is being given to modify plants to fit the restrictive growing conditions imposed by salinity. If economically important crops could be manipulated and made salt resistant, this land could be farmed resulting in greater sales of seed and greater yield of useful crops. Conventional breeding for salt tolerance has been attempted for a long time. These breeding practices have been based mainly on the following strategies: a) the use of wide crosses between crop plants and their more salt-tolerant wild relatives (Rush and Epstein, *J. Amer. Hort. Sci.*, 106:699-704 (1981)), b) screening and selecting for variation within a particular phenotype (Norlyn, in *Genetic Engineering of Osmoregulation*, pp. 293-309 (1980)), c) designing new phenotypes through recurrent selection (Tal, *Plant & Soil*, 89:199-226 (1985)). The lack of success in generating tolerant varieties (given the low number of varieties released and their limited salt tolerance) (Flowers and Yeo, *Aust. J, Plant. Physiol.*, 22:875-884 (1995)) would suggest that conventional breeding practices are not enough and that in order to succeed a breeding program should include the engineering of transgenic crops (Bonhert and Jensen, *Aust. J. Plant. Physiol.*, 23:661-667 (1996)).

Several biochemical pathways associated with stress tolerance have been characterized in different plants and a few of the genes involved in these processes have been identified and in some cases the possible role of proteins has been investigated in transgenic/overexpression experiments. Several compatible solutes have been proposed to play a role in osmoregulation under stress. Such compatible solutes, including carbohydrates (Tarcynski et al., *Science*, 259:508-510 (1995)), amino acids (Kishor et al., *Plant Physiol.*, 108:1387-1394 (1995)) and quaternary N-compounds (Ishtani et al., *Plant Mol. Biol.*, 27:307-317 (1995)) have been shown to increase osmoregulation under stress. Also, proteins that are normally expressed during seed maturation (LEAs, Late Embriogenesis Abundant proteins) have been suggested to play a role in water retention and in the protection of other proteins during stress. The overexpression of LEA in rice provided a moderate benefit to the plants during water stress (Xu et al., *Plant Physiol.*, 110:249-257 (1996), and Wu and Ho, WO 97/13843).

A single gene (sod2) coding for a $Na^+/H^+$ antiport has been shown to confer sodium tolerance in fission yeast (Jia et al., *EMBO J.*, 11:1631-1640 (1992) and Young and Zheng, WO 91/06651), although the role of this plasma membrane-bound protein appears to be only limited to yeast. One of the main disadvantages of using this gene for transformation of plants is associated with the typical problems encountered in heterologous gene expression, i.e. incorrect folding of the gene product, targeting of the protein to the target membrane and regulation of the protein function.

$Na^+/H^+$ antiporters with vacuolar antiport activity have been identified in red beet storage tissue and a variety of halophytic and salt-tolerant glycophtic plant species (Barkla and Pantoja, *Ann. Rev. Plant. Physiol.* 47:159 (1996), and Blumwald and Gelli, *Adv. Bot. Res.* 25:401 (1997)). More recently, a gene encoding a vacuolar $Na^+/H^+$ antiporter from *Arabadopsis thaliana*, designated AtNHX1, has been isolated (Blumwald et al., WO 99/47679). Overexpression of this gene in *Arabadopsis*, tomato, and canola has been shown to enhance salt tolerance in transgenic plants (Apse et al., *Science*, 285:1256-1258 (1999), Zhang and Blumwald, *Nat. Biotechnol*, 19:765-768 (2001), and Zhang et al., *PNAS USA*, 98:12832-12836 (2001)).

BRIEF SUMMARY OF THE INVENTION

The present invention provides methods of enhancing salt tolerance in plants by the introduction of a polynucleotide encoding a $Na^+/H^+$ transporter polypeptide, which when expressed confers increased salt tolerance in the plant. Each of these polypeptides have an amino acid sequence at least 80% identical to SEQ ID NO:2 and fewer than 530 amino acids.

In some aspects of the invention, the method includes the introduction of a polynucleotide having a sequence consisting of SEQ ID NO: 5, 7, 9, 11, 13 or 15 to confer the salt tolerance to the plant.

In some aspects of the invention the method includes the introduction of a polynucleotide encoding a polypeptide having a sequence consisting of SEQ ID NO:6, 8, 10, 12 or 14 to confer salt tolerance to the plant.

In some aspects of the invention, the method includes the introduction of a polynucleotide which encodes a polypeptide of less than 500, or less than 475 amino acids in length to confer the salt tolerance to the plant.

In an alternative embodiment, the method for enhancing salt tolerance of a plant comprises introducing into the plant a polynucleotide encoding a Na+/H+ transporter polypeptide with an amino acid sequence at least 80% identical to SEQ ID NO:2 in which in the residue corresponding to the serine at position 508 in SEQ ID NO:2 is replaced by an amino acid that confers the increased salt tolerance of the Na+/H+ transporter polypeptide.

In some embodiments, a neutral or polar amino acid replaces the serine at position 508 in SEQ ID NO:2.

In some embodiments, the neutral or polar amino acid corresponding to the serine at position 508 in SEQ ID NO:2 is threonine, methionine, cysteine, asparagine or glutamine.

In some embodiments, the purified polynucleotide sequence encoding a $Na^+/H^+$ transporter polypeptide conferring salt tolerance is SEQ ID NOS:3.

In some embodiments, the $Na^+/H^+$ transporter polypeptide sequence encoded by the purified polynucleotide is SEQ ID NO:4.

The present invention also provides for transgenic plants comprising a polynucleotide encoding a Na+/H+ transporter polypeptide, which when expressed confers increased salt tolerance in the plant; and wherein the transporter polypeptide comprises an amino acid sequence at least 80% identical to SEQ ID NO:2 of fewer than 530 amino acids.

In some aspects of the invention, the transgenic plants comprising a Na+/H+ transporter polypeptide conferring increased salt tolerance in the plant has an amino acid sequence at least 80% identical to SEQ ID NO:2, and the residue corresponding to the serine at position 508 in SEQ ID NO:2 is replaced by an amino acid that confers the increased salt tolerance. In some aspects of the invention, the replacement amino acid is a polar or neutral amino acid, such as cysteine.

Definitions

The term "plant" includes whole plants, shoot vegetative organs and/or structures (e.g. leaves, stems and tubers), roots, flowers and floral organs (e.g. bracts, sepals, petals, stamens, carpels, anthers), ovules (including egg and central cells), seed (including zygote, embryo, endosperm, and seed coat), fruit (e.g., the mature ovary), seedlings, plant tissue (e.g. vascular tissue, ground tissue, and the like), cells (e.g. guard cells, egg cells, trichomes and the like), and progeny of same. The class of plants that can be used in the method of the invention is generally as broad as the class of higher and lower plants amenable to transformation techniques, including angiosperms (monocotyledonous and dicotyledonous plants), gymnosperms, ferns, and multicellular algae. It includes plants of a variety of ploidy levels, including aneuploid, polyploid, diploid, haploid and hemizygous.

The phrase "nucleic acid sequence" refers to a single or double-stranded polymer of deoxyribonucleotide or ribonucleotide bases read from the 5' to the 3' end. It includes chromosomal DNA, self-replicating plasmids, infectious polymers of DNA or RNA and DNA or RNA that performs a primarily structural role.

The phrase "heterologous sequence" refers to a sequence that originates from a foreign species, or, if from the same species, is modified from its original form. For example, a promoter operably linked to a heterologous coding sequence refers to a coding sequence from a species different from that from which the promoter was derived, or, if from the same species, a coding sequence which is not naturally associated with the promoter (e.g. a genetically engineered coding sequence or an allele from a different ecotype or variety).

A polynucleotide "exogenous to" an individual plant is a polynucleotide which is introduced into the plant by any means other than by a sexual cross. Examples of means by which this can be accomplished are described below, and include Agrobacterium-mediated transformation, biolistic methods, electroporation, and the like. Such a plant containing the exogenous nucleic acid is referred to here as a T1 (e.g. in *Arabidopsis* by vacuum infiltration) or R0 (for plants regenerated from transformed cells in vitro) generation transgenic plant. Transgenic plants that arise from sexual cross or by selfing are descendants of such a plant.

An "NHX1 nucleic acid" or "NHX1 polynucleotide sequence" of the invention is a subsequence or full length polynucleotide which, encodes a NHX1 polypeptide and its complement, e.g. SEQ ID NOS:1, 3, 5, 7, 9, 11, 13, or 15. One example of an NHX1 gene, from *Arabadopsis*, is AtNHX1. The NHX1 gene products of the invention (e.g. mRNAs or polypeptides) are characterized by the ability to confer increased salt tolerance. A NHX1 polynucleotide of the invention typically comprises a coding sequence of at least about 250 nucleotides to about 2000 nucleotides in length. Usually the NHX1 nucleic acids of the invention are from about 400 to about 1600 nucleotides.

In the expression of transgenes one of skill will recognize that the inserted polynucleotide sequence need not be identical and may be "substantially identical" to a sequence of the gene from which it was derived. As explained below, these variants are specifically covered by this term.

In the case where the inserted polynucleotide sequence is transcribed and translated to produce a functional NHX1 polypeptide, one of skill will recognize that because of codon degeneracy, a number of polynucleotide sequences will encode the same polypeptide. These variants are specifically covered by the terms "NHX1 polynucleotide sequence" or "NHX1 polynucleotide sequence". In addition, the terms specifically include those full length sequences substantially identical (determined as described below) with an NHX1 gene sequence and that encode proteins that retain the function of the encoded proteins. Thus, in the case of the *Arabidopsis* AtNHX1 gene disclosed here, the above term includes variant polynucleotide sequences which have substantial identity with the sequences disclosed here and which encode proteins capable of conferring salt tolerance on a transgenic plant comprising the sequence.

Two polynucleotides or polypeptides are said to be "identical" if the sequence of nucleotides or amino acid residues, respectively, in the two sequences is the same when aligned for maximum correspondence as described below. The term "complementary to" is used herein to mean that the complementary sequence is identical to all or a portion of a reference polynucleotide sequence.

Sequence comparisons between two (or more) polynucleotides or polypeptides are typically performed by comparing sequences of the two sequences over a segment or "comparison window" to identify and compare local regions of sequence similarity. The segment used for purposes of comparison may be at least about 20 contiguous positions, usually about 50 to about 200, more usually about 100 to about 150 in which a sequence may be compared to a reference sequence of the same number of contiguous positions after the two sequences are optimally aligned.

Optimal alignment of sequences for comparison may be conducted by the local homology algorithm of Smith and Waterman Adv. Appl. Math. 2: 482 (1981), by the homology alignment algorithm of Needleman and Wunsch J. Mol. Biol. 48:443 (1970), by the search for similarity method of Pearson and Lipman Proc. Natl. Acad. Sci. (U.S.A.) 85: 2444 (1988), by computerized implementations of these algorithms (GAP, BESTFIT, FASTA, and TFASTA in the Wisconsin Genetics Software Package, Genetics Computer Group (GCG), 575 Science Dr., Madison, Wis.), or by inspection. "Percentage of sequence identity" is determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The term "substantial identity" of polynucleotide sequences means that a polynucleotide comprises a sequence that has at least 60% sequence identity, preferably at least 80%, more preferably at least 90% and most preferably at least 95%, compared to a reference sequence using the programs described above (preferably BESTFIT) using standard parameters. One of skill will recognize that these values can be appropriately adjusted to determine corresponding identity of proteins encoded by two nucleotide sequences by taking into account codon degeneracy, amino acid similarity, reading frame positioning and the like. Substantial identity of amino acid sequences for these purposes normally means sequence identity of at least 40%, preferably at least 60%, more preferably at least 90%, and most preferably at least 95%. Polypeptides which are "substantially similar" share sequences as noted above except that residue positions which are not identical may differ by conservative amino acid changes. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, and asparagine-glutamine.

Another indication that nucleotide sequences are substantially identical is if two molecules hybridize to each other under stringent conditions. Stringent conditions are sequence dependent and will be different in different circumstances. Generally, stringent conditions are selected to be about 5° C. to about 20° C. lower than the thermal melting point (Tm) for the specific sequence at a defined ionic strength and pH. The Tm is the temperature (under defined ionic strength and pH) at which 50% of the target sequence hybridizes to a perfectly matched probe. Typically, stringent conditions will be those in which the salt concentration is about 0.02 molar at pH 7 and the temperature is at least about 60° C. However, nucleic acids which do not hybridize to each other under stringent conditions are still substantially identical if the polypeptides which they encode are substantially identical. This may occur, e.g., when a copy of a nucleic acid is created using the maximum codon degeneracy permitted by the genetic code.

As used herein, a homolog of a particular NHX1 gene (e.g., the *Arabidopsis* AtNHX1 genes disclosed here) is a second gene (either in the same species or in a different species) which has a polynucleotide sequence of at least 50 contiguous nucleotides which are substantially identical (determined as described above) to a sequence in the first gene. It is believed that, in general, homologs share a common evolutionary past.

DETAILED DESCRIPTION OF THE INVENTION

Figure 1:
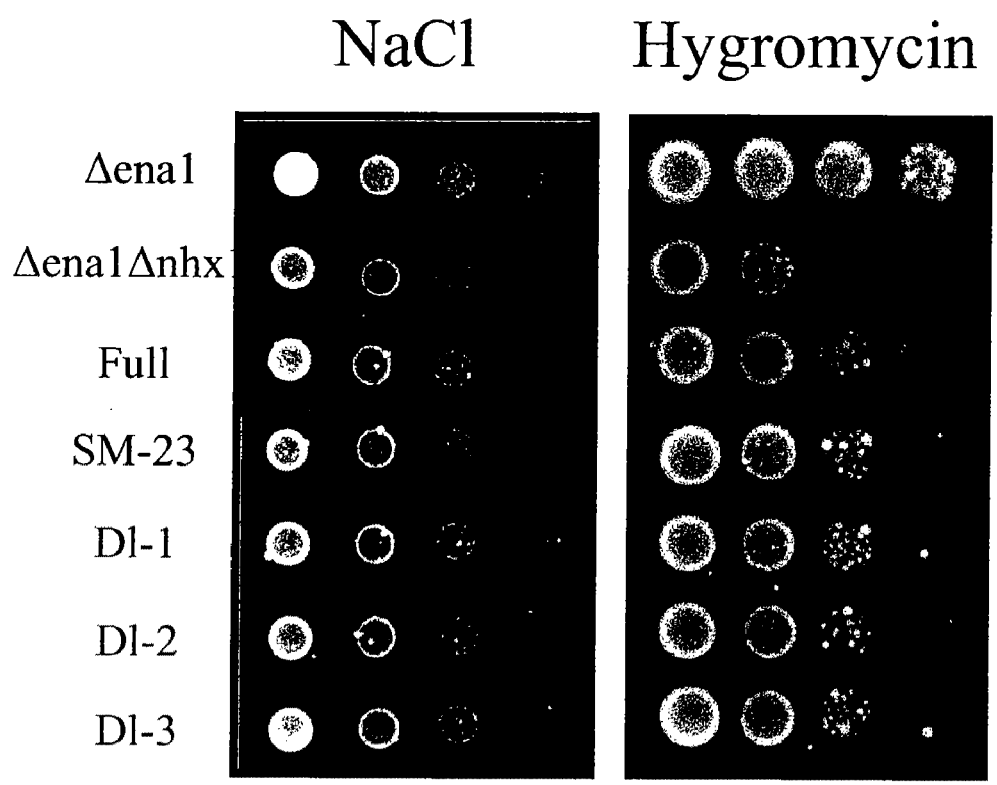
FIG. 1 shows yeast transformation assay results indicating modified AtNHX1 increases salt tolerance.

The present invention provides novel modified isolated nucleic acid molecules encoding proteins for the transport of sodium ions across a membrane of a cell, for example, from the cytosol of a cell into a vacuole, provide the cell with salt tolerance.

NHX1 genes encode membrane bound Na+/H+ antiport transporters that conduct $Na^+$ across a membrane using an electrochemical gradient of protons, generated, for example, by vacuolar H+-adenosine triphosphatase (ATPase) and H+-inorganic pyrophosphatase ($PP_i$ase). In the present invention, mutated and truncated forms of NHX1 containing augmented transport activity have been created. The modified gene products (proteins) allow more accumulation of sodium ions from the cytosol into the intracellular compartments, such as the vacuole, compared with the entire protein. These genes allow for the engineering of salt tolerant plants by transformation of salt-sensitive crops overexpressing this gene.

The invention also includes modified $Na^+/H^+$ antiporters having changed ion selectivity or ionic permeability leading to increased salt or drought or osmotic tolerance.

The invention also relates to the modification of NHX1 genes by using site-directed mutagenesis and deletions based on PCR amplification to screen the modified protein forms with increased transport activity or changed ion selectivity.

Isolation of Nucleic Acids of the Invention

Generally, the nomenclature and the laboratory procedures in recombinant DNA technology described below are those well known and commonly employed in the art. Standard techniques are used for cloning, DNA and RNA isolation, amplification and purification. Generally enzymatic reactions involving DNA ligase, DNA polymerase, restriction endonucleases and the like are performed according to the manufacturer's specifications. These techniques and various other techniques are generally performed according to Sambrook et al., *Molecular Cloning-A Laboratory Manual, Cold Spring Harbor Laboratory*, Cold Spring Harbor, N.Y., (1989) or *Current Protocols in Molecular Biology*, Volumes 1-3, John Wiley & Sons, Inc. (1994-1998).

Using the sequences provided here, the isolation of NHX1 nucleic acids may be accomplished by a number of techniques. For instance, oligonucleotide probes based on the sequences disclosed here can be used to identify the desired gene in a cDNA or genomic DNA library. To construct genomic libraries, large segments of genomic DNA are generated by random fragmentation, e.g. using restriction endonucleases, and are ligated with vector DNA to form concatemers that can be packaged into the appropriate vector. To prepare a cDNA library, mRNA is isolated from the desired organ, such as flowers, and a cDNA library which contains the NHX1 gene transcript is prepared from the mRNA. Alternatively, cDNA may be prepared from mRNA extracted from other tissues in which AtNHX1 genes or homologs are expressed.

The cDNA or genomic library can then be screened using a probe based upon the sequence of a cloned NHX1 gene or fragment thereof disclosed here. Probes may be used to hybridize with genomic DNA or cDNA sequences to isolate homologous genes in the same or different plant species. Alternatively, antibodies raised against a NHX1 polypeptide or fragment thereof can be used to screen a mRNA expression library.

Alternatively, the nucleic acids of interest can be amplified from nucleic acid samples using amplification techniques. For instance, polymerase chain reaction (PCR) technology can be used to amplify the sequences of the NHX1 genes directly from genomic DNA, from cDNA, from genomic libraries or cDNA libraries. PCR and other in vitro amplification methods may also be useful, for example, to clone nucleic acid sequences that code for proteins to be expressed, to make nucleic acids to use as probes for detecting the presence of the desired mRNA in samples, for nucleic acid sequencing, or for other purposes. For a general overview of PCR see PCR Protocols: A Guide to Methods and Applications. (Innis, M, Gleaned, D., Sninsky, J. and White, T., eds.), Academic Press, San Diego (1990).

Polynucleotides may also be synthesized by well-known techniques as described in the technical literature. See, e.g., Carruthers et al., *Cold Spring Harbor Symp. Quant. Biol.*, 47:411-418 (1982), and Adams et al., *J. Am. Chem. Soc.*, 105:661 (1983). Double stranded DNA fragments may then be obtained either by synthesizing the complementary strand and annealing the strands together under appropriate conditions, or by adding the complementary strand using DNA polymerase with an appropriate primer sequence.

NHX1 nucleic acids of interest may also be identified by searching nucleic acid databases, e.g., EST databases and identifying sequences with high similarity to a known NHX1 nucleic acid sequence. Once a candidate NHX1 nucleic acid or polynucleotide sequence of the invention has been identified, standard methods can be used to determine if the putative nucleic acid is a NHX1 nucleic acid of the invention. Methods of assaying for NHX1 activity are known in the art, e.g., see example 1 and Apse et al., *Science*. 285, 1256-1258.

Preparation of Recombinant Vectors

To use isolated sequences for transformation and other molecular biological techniques, recombinant DNA vectors suitable for transformation of plant cells are prepared. Techniques for transforming a wide variety of higher plant species are well known and described in the technical and scientific literature. See, for example, Weising et al. *Ann. Rev. Genet.*, 22:421-477 (1988). A DNA sequence coding for the desired polypeptide, for example a cDNA sequence encoding a full length protein, will preferably be combined with transcriptional and translational initiation regulatory sequences which will direct the transcription of the sequence from the gene in the intended tissues of the transformed plant.

For example, for overexpression, a plant promoter fragment may be employed which will direct expression of the gene in all tissues of a regenerated plant. Such promoters are referred to herein as "constitutive" promoters and are active under most environmental conditions and states of development or cell differentiation. Examples of constitutive promoters include the cauliflower mosaic virus (CaMV) 35S transcription initiation region, the 1'- or 2'-promoter derived from T-DNA of *Agrobacterium tumafaciens*, and other transcription initiation regions from various plant genes known to those of skill. Such genes include for example, ACT11 from *Arabidopsis* (Huang et al. *Plant Mol. Biol.*, 33:125-139 (1996)), Cat3 from *Arabidopsis* (GenBank No. U43147, Zhong et al., *Mol. Gen. Genet.*, 251:196-203 (1996)), the gene encoding stearoyl-acyl carrier protein desaturase from *Brassica napus* (Genbank No. X74782, Solocombe et al. *Plant Physiol.*, 104:1167-1176 (1994)), GPc1 from maize (GenBank No. X15596, Martinez et al. *J. Mol. Biol*, 208:551-565 (1989)), and Gpc2 from maize (GenBank No. U45855, Manjunath et al., *Plant Mol. Biol.*, 33:97-112 (1997)).

Alternatively, the plant promoter may direct expression of the NHX1 nucleic acid in a specific tissue, organ or cell type (i.e. tissue-specific promoters, organ-specific promoters) or may be otherwise under more precise environmental or developmental control (i.e. inducible promoters). Examples of environmental conditions that may effect transcription by inducible promoters include anaerobic conditions, elevated temperature, the presence of light, or sprayed with chemicals/hormones. One of skill will recognize that an organ-specific promoter may drive expression of operably linked sequences in organs other than the target organ. Thus, as used herein an organ-specific promoter is one that drives expression preferentially in the target organ, but may also lead to some expression in other organs as well.

A number of tissue-specific promoters can also be used in the invention. For instance, root promoters that direct expression of root tissue nucleic acids are of particular importance to the current invention.

If proper polypeptide expression is desired, a polyadenylation region at the 3'-end of the coding region should be included. The polyadenylation region can be derived from the natural gene, from a variety of other plant genes, or from T-DNA.

The vector comprising the sequences (e.g., promoters or coding regions) from genes of the invention will typically comprise a marker gene that confers a selectable phenotype on plant cells. For example, the marker may encode biocide resistance, particularly antibiotic resistance, such as resistance to kanamycin, G418, bleomycin, hygromycin, or herbicide resistance, such as resistance to chlorosulfuron or Basta.

Production of Transgenic Plants

DNA constructs of the invention may be introduced into the genome of the desired plant host by a variety of conventional techniques. For example, the DNA construct may be introduced directly into the genomic DNA of the plant cell using techniques such as electroporation and microinjection of plant cell protoplasts, or the DNA constructs can be introduced directly to plant tissue using biolistics, e.g., DNA particle bombardment.

Microinjection techniques are known in the art and well described in the scientific and patent literature. The introduction of DNA constructs using polyethylene glycol precipitation is described in Paszkowski et al. *Embo J.*, 3:27 17-2722 (1984). Electroporation techniques are described in Fromm et al. *Proc. Natl. Acad. Sci. USA*, 82:5824 (1985). Biolistic transformation techniques are described in Klein et al. *Nature*, 327:70-73 (1987).

Alternatively, the DNA constructs may be combined with suitable T-DNA flanking regions and introduced into a conventional *Agrobacterium tumefaciens* host vector. The virulence functions of the *Agrobacterium tumefaciens* host will direct the insertion of the construct and adjacent marker into the plant cell DNA when the cell is infected by the bacteria. *Agrobacterium tumefaciens*-mediated transformation techniques, including disarming and use of binary vectors, are well described in the scientific literature. See, for example Horsch et al. *Science*, 233:496-498 (1984), and Fraley et al. *Proc. Natl. Acad. Sci. USA*, 80:4803 (1983) and Gene Transfer to Plants, Potrykus, ed. (Springer-Verlag, Berlin 1995).

Transformed plant cells which are derived by any of the above transformation techniques can be cultured to regenerate a whole plant which possesses the transformed genotype and thus the desired phenotype such as decreased farnesyltransferase activity. Such regeneration techniques rely on manipulation of certain phytohormones in a tissue culture growth medium, typically relying on a biocide and/or herbicide marker that has been introduced together with the desired nucleotide sequences. Plant regeneration from cultured protoplasts is described in Evans et al., *Protoplasts Isolation and Culture, Handbook of Plant Cell Culture*, pp. 124-176, MacMillilan Publishing Company, New York, 1983; and Binding, *Regeneration of Plants, Plant Protoplasts*, pp. 21-73, CRC Press, Boca Raton, 1985. Regeneration can also be obtained from plant callus, explants, organs, or parts thereof. Such regeneration techniques are described generally in Klee et al., *Ann. Rev, of Plant Phys.*, 38:467-486 (1987).

The nucleic acids of the invention can be used to confer desired traits on essentially any plant. Thus, the invention has use over a broad range of plants, including species from the genera *Anacardium, Arachis, Asparagus, Atropa, Avena, Brassica, Chlamydomonas, Chlorella, Citrus, Citrullus, Capsicum, Carthamus, Cocos, Coffea, Cucumis, Cucurbita, Cyrtomium, Daucus, Elaeis, Fragaria, Glycine, Gossypium, Helianthus, Heterocallis, Hordeum, Hyoscyamus, Lactuca, Laminaria, Linum, Lolium, Lupinus, Lycopersicon, Macrocystis, Malus, Manihot, Majorana, Medicago, Nereocystis, Nicotiana, Olea, Oryza, Osmunda, Panieum, Pannesetum, Persea, Phaseolus, Pistachia, Pisum, Pyrus, Polypodium, Prunus, Pteridium, Raphanus, Ricinus, Secale, Senecio, Sinapis, Solanum, Sorghum, Theobromus, Trigonella, Triticum, Vicia, Vitis, Vigna*, and *Zea*.

One of skill will recognize that after the expression cassette is stably incorporated in transgenic plants and confirmed to be operable, it can be introduced into other plants by sexual crossing. Any of a number of standard breeding techniques can be used, depending upon the species to be crossed.

Using known procedures one of skill can screen for plants of the invention by detecting the increase or decrease of NHX1 mRNA or protein in transgenic plants. Means for detecting and quantifying mRNAs or proteins are well known in the art, e.g., Northern Blots, Western Blots or activity assays. The plants of the invention can also be identified by detecting the desired phenotype. For instance, measuring salt tolerance or drought tolerance using methods as described below.

Detection of Transgenic Organisms of the Invention

Transformed yeast strains containing the polynucleotides of the invention can be analyzed using established molecular biology techniques as well as by monitoring growth rates using culture medium selective for a wide variety of phenotypes including salt toelrance.

Alternatively, transgenic plants comprising the invention may be the subject of analysis. After preparation of the expression cassettes containing the polynucleotides of the present invention and introduction of the cassettes into a plant, the resultant transgenic plants can be assayed for the phenotypical characteristics associated with increased or decreased NHX1 expression. For example, after introduction of the cassette into a plant, the plants are screened for the presence of the transgene and crossed to an inbred or hybrid line. Progeny plants are then screened for the presence of the transgene and self-pollinated. Progeny from the self-pollinated plants are grown. The resultant transgenic plants can be assayed for increased salt tolerance and increased drought tolerance, and decreased sensitivity to toxins. For example, a transgenic plant can be assayed for increased salt tolerance or drought tolerance. Methods for assaying for increased salt tolerance are known and include measuring the growth rate of plants at increasing salt concentrations. Plant biomass, root/shoot ratios, and tissue ion content. Root and hypocotyl growth rates can are measured and correlated with tissue water content of plants growing at different salt concentrations. Methods for assaying increased drought tolerance are also well established and include measuring transpiration rates of transgenic plant tissues, stomatal conductance, rate of water loss in a detached leaf assay or examining leaf turgor. Transgenic plants with decreased transpiration rates, for example, have increased drought tolerance.

EXAMPLES

Example 1

Site-Directed Mutagenesis and Cloning of Truncated ATNHX1

The full length cDNA of AtNHX1 was obtained by RT-PCR and cloned into pCR2.1-TOPO vctor (Invitrogen). The sequence was confirmed by sequencing the full open reading frame. The full length cDNA was then subcloned into yeast vector pYPGE15 by using BamH1 and EcoR1 cloning sites. Site-directed mutagenesis was carried out by following the instruction of QuikChange Site-Directed Mutagenesis Kit (Stratagene). The primes that was used for generation SM-23 are as follows: SM-23-F, ggagacaatttgatgactgcttcatgcgacccgtc; (SEQ ID NO:17); SM-23-R, gacgggtcgcatgaagcagtcatcaaattgtctcc (SEQ ID NO: 18). For the cloning of truncated AtNHX1, the truncated cDNA was amplified by PCR and cloned into pYPGE15 vector. The primers for the truncated AtNHX1 cloning are as follows: EXCH-5, agctaggatccggatctagaagaagataacaatgttgg (SEQ ID NO: 19); EXCH-DL-1, agctgaattcctagggtacaaagccacgacctc (SEQ ID NO:20); EXCH-DL-2, agctgaattcctacaagaagccacgtatactg (SEQ ID NO:21); EXCH-DL-3, agctgaattcctaagataacatgctcgtggtg (SEQ ID NO:22). All sequence were verified by sequencing.

Example 2

Yeast Transformation and Drop Tests

The yeast cells were transformed using lithium acetate/PEG method. Yeast cells were inoculated into drop-out liquid medium and cultured overnight at 30° C. The cells were harvested by centrifuge and resuspended into APG medium (Rodriguez-Navarro and Ramos, *J. Bacteriol.*, 159:940-945 (1984)) and adjusted the OD600 to 1.0. Serial 10 times dilutions were made and 3 l of the cells were loaded onto APG medium with different salt supplements, or onto YPD (1% yeast extract, 2% peptone, 2% glucose) medium with 10 mg/L hygromycin.

Example 3

Increased Salt Tolerance Conferred by Modified ATNHX1

As shown in FIG. 1, the yeast mutant strain (ena1 nhx1) lacking endogenous NHX1 $Na^+/H^+$ antiporter was more sensitive to NaCl as well as hygromycin than the control strain (ena1). Expression of AtNHX1 in the yeast mutant partially recovered the mutant phenotype, indicating that AtNHX1 functions as $Na^+/H^+$ antiporter to compartment $Na^+$ into vacuole. The modified AtNHX1, including SM-23, Dl-1, Dl-2, and Dl-3, conferred yeast mutant cell more tolerance to salt and hygromycin than the complete form. This result suggests that the modified AtNHX1 have higher antiport activity and could transport more $Na^+$ into vacuole.

Example 4

Changed Ion Selectivity of Modified ATNHX1

Figure 2:
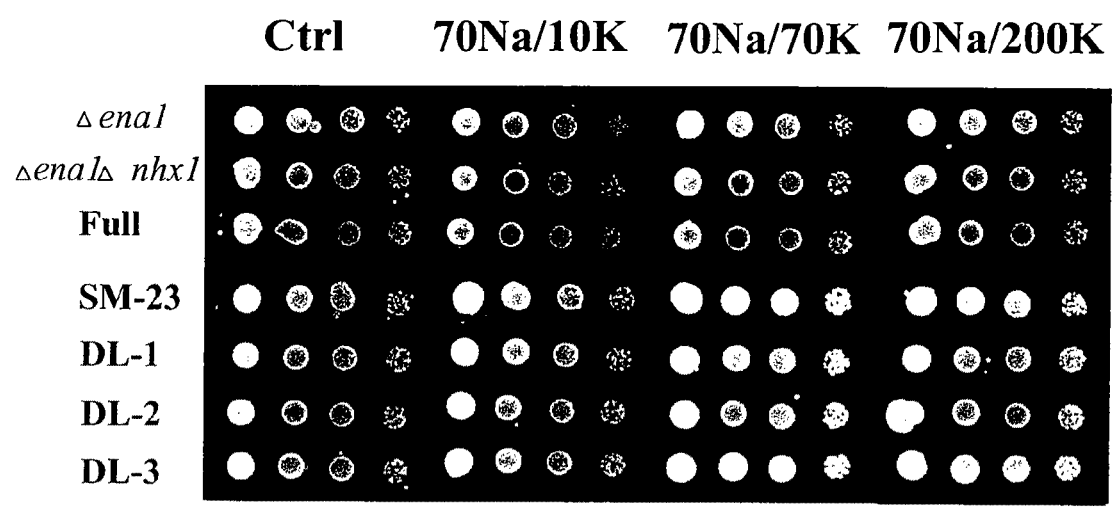
FIG. 2 shows yeast tranformation assay results showing C-terminal deletions of AtNHX1 control $Na^+/K^+$ selectivity of the transporter.

When grown on the APG medium without NaCl, the yeast cells grew equally regardless expression of complete or modified AtNHX1 (FIG. 2). However, the yeast cells expressing modified AtNHX1 showed higher tolerance to NaCl than that expressing complete form of AtNHX1, when increasing $K^+$ in the medium. This result suggests that the C-terminus of NHX1 genes control the $Na^+/K^+$ selectivity.

Example 5

Increased $LI^+$ Tolerance Conferred by Modified ATNHX1

Figure 3:
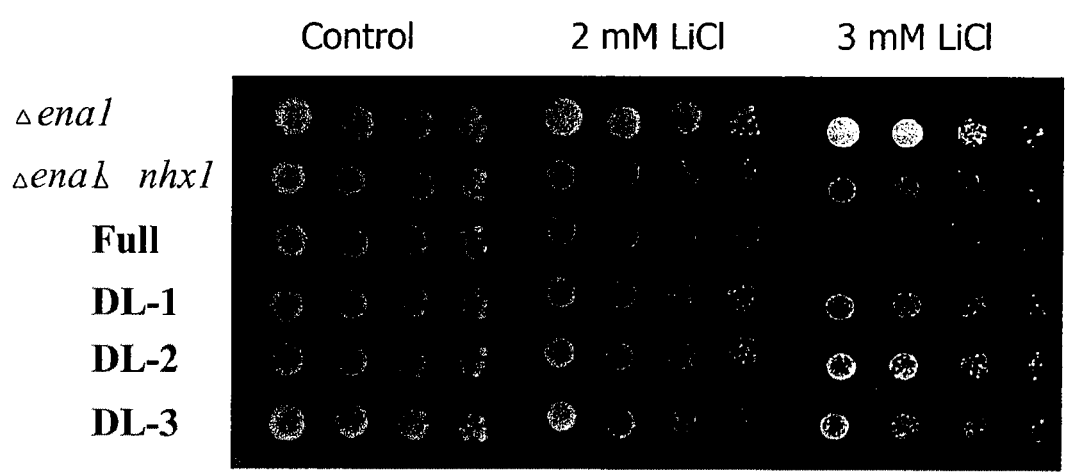
FIG. 3 shows yeast transformation assay results indicating modified AtNHX1 increases $Li^+$ tolerance.

The yeast NHX1 can transport both $Na^+$ and $Li^+$. The yeast mutant lacking NHX1 gene is more sensitive to Li+ than the control yeast strain (FIG. 3). Although AtNHX1 could rescue the $Na^+$ sensitive phenotype of yeast mutant (FIG. 1), AtNHX1 was unable to restore the $Li^+$ sensitive phenotype of the yeast mutant as shown in FIG. 3, indicating that AtNHX1 has little or no activity for $Li^+$ transport. Surprisingly, the yeast mutant cells expressing modified AtNHX1 displayed $Li^+$ tolerance almost to the level of control yeast strain. This result provides a possibility to modify transporters capable to detoxify different ions, and to engineer plants to be able to tolerance different toxic ions when overexpressing the modified transporters.

Example 6

Elevated Tolerance to Osmotic Stress in Yeast Expressing Modified ATNHX1

Figure 4:
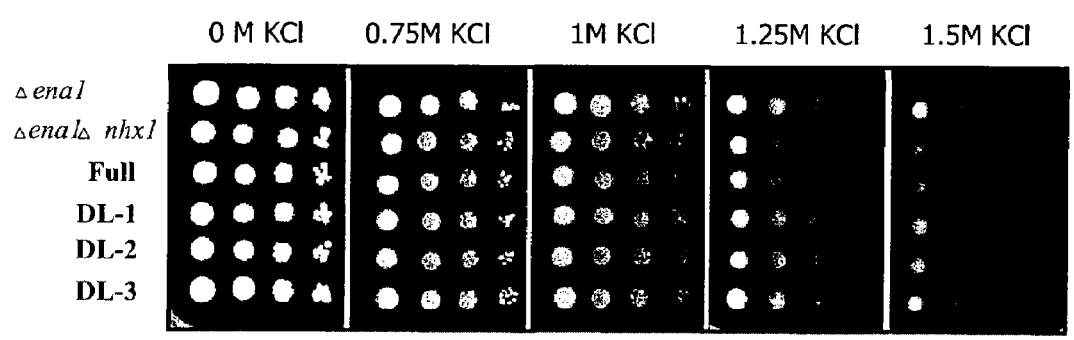
FIG. 4 shows yeast transformation assay results indicating modified AtNHX1 increases tolerance to osmotic stress.

Vacuolar $Na^+/H^+$ antiporter can sequestrate $Na^+$ into vacuole and keep the turgor pressure of the cell. The regulation of turgor pressure may function to drive water flow into the cell under osmotic stress. The yeast mutant cells lacking of NHX1 showed sensitive phenotype after adding over 1 M KCl to the growth medium (FIG. 4), suggesting that NHX1 is also important in osmotic regulation. Since $Na^+$ was absent in the growth medium, the osmotic regulation by NHX1 was possibly fulfilled by transport of $K^+$ into vacuole. Expression of complete form of AtNXH1 could not complement the mutant phenotype, but modified forms of AtNHX1 rescued the mutant cells growth to the level as wild type (ena1) did, indicating that modified forms of AtNHX1 have higher $K^+$ transport activity than the complete form.

It is possible to use the modified forms of NHX1 to engineer plants to be more drought tolerance. Since the modified forms of AtNHX1 could transport more $K^+$ into vacuole, the higher concentration of $K^+$ in vacuole could drive water uptake into the cell, which would generate higher strength to force more water flow through xylem stream. Theoretically, the transgenic plants overexpressing these modified forms of AtNHX1 could take up water more effectively, and more tolerance to drought stress.

Example 7

Modified NHX1

Figure 5:
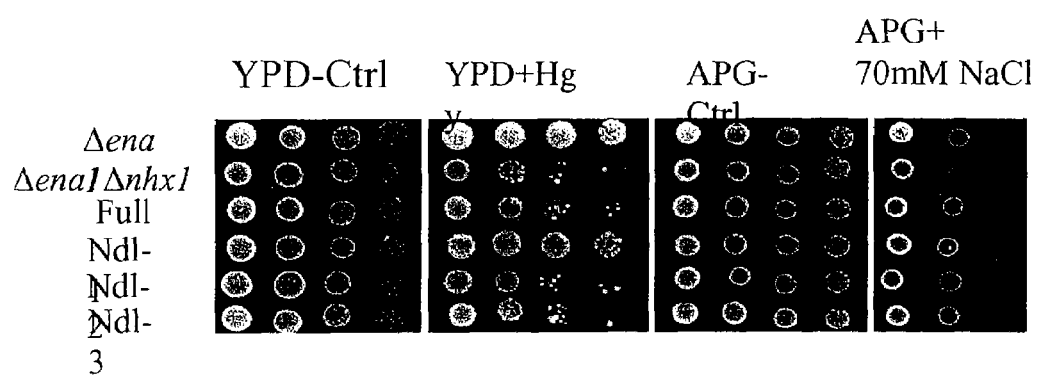
FIG. 5 shows the results of yeast transformation assays performed to characterize activity of AtNHX1 N-terminus and tranmembrane domains
Figure 6:
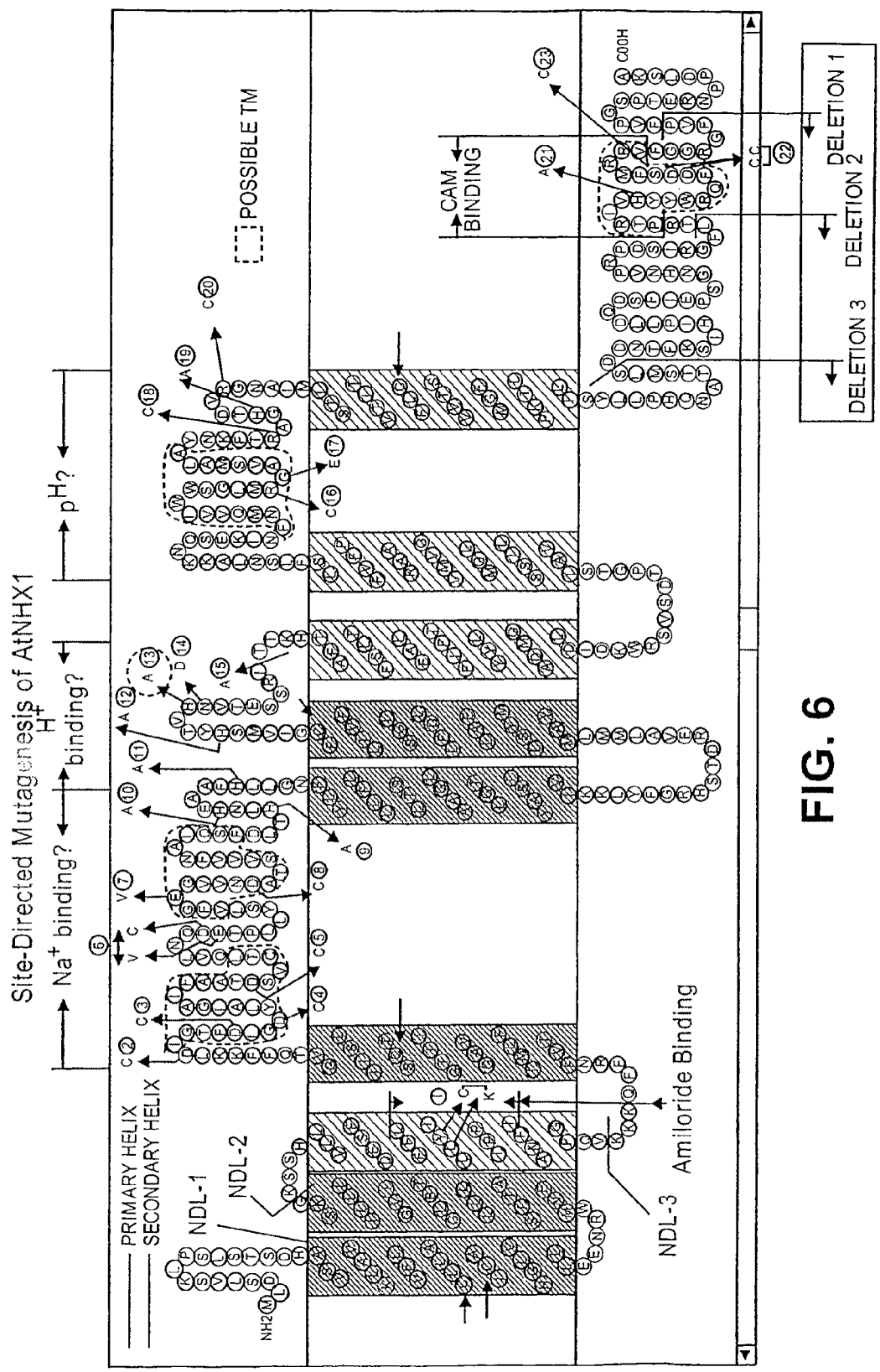
FIG. 6 shows the sites of site-directed mutagenesis and truncation of AtNHX1 conferring salt tolerance.

Using the methods described previously in Examples 1 and 2, modified NHX1 polynucleotides including 23 site mutations, 3 N-terminus deletions, and 3 C-terminus deletions of ATNHX1 cDNA were generated (See Table 1, and FIG. 5). The modified AtNHX1 cDNAs in yeast vector were transferred into a yeast mutant lacking endogenous $Na^+/H^+$ antiporter NHX1 and $Na^+$ pump ENA1-4. The activities and ion selectivity of the transformants were determined by testing the growth of yeast harboring distinct forms of AtNHX1 under different growth conditions.

TABLE 1

| Name | Mutation | Growth |
|---|---|---|
| Full | NA | ++++ |
| SM-1 | Y85C/L86R | + |
| SM-2 | D137C | +++++ |
| SM-3 | D142C | + |
| SM-4 | D145C | ++++ |
| SM-5 | D157C | ++++ |
| SM-6 | D168C/E169V | ++++ |
| SM-7 | E180V | ++++ |
| SM-8 | D185C | +++ |
| SM-9 | H202A | +++ |
| SM-10 | H205A | ++++ |
| SM-11 | H210A | ++++ |
| SM-12 | H285A | ++++ |
| SM-13 | H289A | ++++ |
| SM-14 | N290D | ++++ |
| SM-15 | H301A | ++++ |
| SM-16 | R390C | ++++ |
| SM-17 | G391E | ++++ |
| SM-18 | R404C | ++++ |
| SM-19 | H407A | ++++ |
| SM-20 | R411C | ++++ |
| SM-21 | H499A | ++++ |
| SM-22 | D506C/D507C | +++++ |

TABLE 1-continued

| Name | Mutation | Growth |
|------|----------|--------|
| SM-23 | S508C | +++++ |
| DL-1 | 17 aa deletion | +++++ |
| DL-2 | 47 aa deletion | +++++ |
| DL-3 | 84 aa deletion | +++++ |
| NDL-1 | 17 aa deletion | +++++++++ |
| NDL-2 | 69 aa deletion | +++ |
| DDL-3 | 98 aa deletion | +++ |

Example 8

Characterization of ATNHX1 N-Terminus and Transmembrane Domains

The functions of the free N-terminus and the first several transmembrane domains of AtNHX1 were characterized using the methods described in Examples 1 and 2 above. Three N-terminal deletion forms of AtNHX1 were created and analyzed in yeast complementation tests. The deletion of the free N-terminus of AtNHX1 (NDL-1, deletion of the first 17 amino acids) conferred yeast mutant strain (Δena1Δnhx1) more tolerant to hygromycin and NaCl compared with the full AtNHX1. The growth of yeast cells expressing NDL-1 was Approximately 30 times higher than that expressing full AtNHX1, indicating that the free N-terminus of AtNHX1 is a negative regulator for antiporter function in yeast cells. The deletion of the first two transmembrane domains (NDL-2) and the deletion of the first three transmembrane domains (NDL-3) abolished the AtNHX1 function on some extend. These results provide the possibility to engineer plant more tolerance to salt by overexpressing modified forms of AtNHX1 with elevated antiport activity, for instance, NDL-1.

REFERENCES

Rush, P W and Epstein, E (1981). J. Amer. Soc. Hort. Sci. 106, 699-704.
Norlyn, J D (1980). In: Genetic Engineering of Osmoregulation (Eds. D W Rains, R C Valentine and A Hollaender) pp. 293-309. Plenum Press: New York.
Tal, M (1985). Plant & Soil 89, 199-226.
Flowers, T J and Yeo, A R (1995). Aust. J. Plant Physiol. 22, 875-884.
Bonhert, H J and Jensen, R G (1996). Aust J. Plant Physiol. 23, 661-667.
Tarcynski, M C, Jensen, R G & Bonhert, H J. (1995) Science 259, 508-510.
Kishor et al. (1995). Plant Physiol. 108, 1387-1394.
Ishitani, M, et al., (1995). Plant Mol. Biol. 27, 307-317
Xu, et al. (1996) Plant Physiol. 110, 249-257.
Wu, R and Ho, THD. Patent # WO9713843.
Jia, Z P, et al., (1992). EMBO J. 11, 1631-1640.
Young, P G & Zheng, P J. Patent #WO9106651.
Ichida, A M & Schroeder, J I. (1996) J. Membrane Biol. 151, 53-62.
Rubio, F. et al., (1999) J. Biol. Chem. 274, 6839-6847.
Liu, W, Schachtman D P & Zhang, W. (2000) J. Biol. Chem. 275, 27924-27932.
Kinclov, O. et al., (2001) Mol. Microbiol. 40, 656-668.
Waditee, R. et al., (2001) J. Biol. Chem. 276, 36931-36938.
Apse, M P. et al., (1999) Science 285, 1256-1258.
Zhang, H X & Blumwald, E. (2001) Nat. Biotechnol. 19, 765-768.
Zhang, H X. et al., (2001) Proc. Natl. Acad. Sci. USA 98, 12832-12836.
Rodriguez-Navarro, A & Ramos, J. (1984) J. Bacteriol. 159, 940-945.
Barkla and Pantoja, (1996) Ann. Rev. Plant. Physiol. 47, 159.
Blumwald and Gelli, (1997) Adv. Bot. Res. 25, 401.

The above examples are provided to illustrate the invention but not to limit its scope. Other variants of the invention will be readily apparent to one of ordinary skill in the art and are encompassed by the appended claims. All publications, patents, and patent applications cited herein are hereby incorporated by reference for all purposes.

1441 gtgcctcggc ctgacagtat acgtggcttc ttgacacggc ccactcgaac cgtgcattac
1501 tactggagac aatttgatga ctccttcatg cgacccgtct ttggaggtcg tggctttgta
1561 ccctttgttc caggttctcc aactgagaga aaccctcctg atcttagtaa ggct
SEQ ID NO:2

Wildtype AtNHX1, protein sequence
MLDSLVSKLPSLSTSDHASVVALN-
LFVALLCACIVLGHLLEENR WMNESITALLIGLGT-
GVTILLISKGKSSHLLVFSEDLFFIYLL-
PPIIFNAGFQVKKKQ
FFRNFVTIMLFGAVGTIISCTIIS-
LGVTQFFKKLDIGTFDLGDYLAIGAIFAATDSVC
TLQVLNQDETPLLYSLVFGEGVVNDATS-
VVVFNAIQSFDLTHLNHEAAFHLLGNFLY LFLL-
STLLGAATGLISAYVIKKLYFGRHST-
DREVALMMLMAYLSYMLAELFDLSGIL
TVFFCGIVMSHYTWHNVTESSRITTKHT-
FATLSFLAETFIFLYVGMDALDIDKWRSVS DTPGT-
SIAVSSILMGLVMVGRAAFVFPLSFLSN-
LAKKNQSEKINFNMQVVIWWSGLM
RGAVSMALAYNKFTRAGHTDVRGNAIM-
ITSTITVCLFSTVVFGMLTKPLISYLLPHQ
NATTSMLSDDNTPKSIHIPLLDQDS-
FIEPSGNHNVPRPDSIRGFLTRPTRTVHYYWRQF
DDS FMRPVFGGRGFVPFVPGSPTERNPPDLSKA
SEQ ID NO:3

SM-23, S508C, single nucleic acid change, cDNA sequence
atgttggattctctagtgtcgaaactgc-
cttcgttatcgacatctgatcacgcttcgtggttgcgttgaatctctttgt tgcact-
tctttgtgcttgtattgttcttggt-
catcttttggaagagaatagatggatgaacgaatccatcaccgccttgt
tgattgggctaggcactggtgttac-
cattttgttgattagtaaaggaaaaagctcgcatcttctcgtctttagtgaagat
cttttcttcatatatcttttgccac-
ccattatattcaatgcagggtttcaagtaaaaaagaagcagtttttccgcaattt
cgtgactattatgcttttggtgctgt-
tgggactattatttcttgcacaatcatatctctaggtgtaacacagttcttta
agaagttggacattggaacctttgact-
tgggtgattatcttgctattggtgccatatttgctgcaacagattcagtatgt
acactgcaggttctgaatcaagacgaga-
cacctttgcttacagtcttgtattcggagagggtgttgtgaatgatgcaac
gtcagttgtggtcttcaacgcgattca-
gagctttgatctcactcacctaaaccacgaagctgcttttcatcttcttggaa act-
tcttgtatttgtttctcctaagtacct-
tgcttggtgctgcaaccggtctgataagtgcgtatgttatcaagaagcta
tactttggaaggcactcaactgac-
cgagaggttgcccttatgatgcttatggcgtatctttcttatatgcttgctgagct
tttcgacttgagcggtatcctcactgt-
gtttttctgtggtattgtgatgtcccattacacatggcacaatgtaacggaga gct-
caagaataacaacaaagcatacctttg-
caactttgtcatttcttgcggagacatttattttcttgtatgttggaatg
gatgccttggacattgacaagtggagatccgtgagtgacacaccgggaa-
catcgatcgcagtgagctcaatcctaatggg tctggtcatggttggaagag-
cagcgttcgtctttccgttatcgtttctatctaacttagccaagaagaatcaaagc-
gaga aaatcaactttaacatgcaggttgt-
gatttggtggtctggtctcatgagaggtgctgtatctatggctcttgcatacaac
aagtttacaagggccgggcacacagatg-
tacgcgggaatgcaatcatgatcacgagtacgataactgtctgtcttttag
cacagtggtgtttggtatgctgac-
caaaccactcataagctacctattaccg-
caccagaacgccaccacgagcatgttat ctgatgacaacaccccaaaatc-
catacatatcccctttgttggaccaagactcgttcattgagccttcagggaaccac-
aat gtgcctcggcctgacagtatacgtggct-
tcttgacacggcccactcgaaccgtgcattactactggacaatttgatga
ctGcttcatgcgacccgtctttggag-
gtcgtggctttgtacccttgttccaggttctccaactgagagaaacctcctg
atcttagtaaggct
SEQ ID NO:4

SM-23, S508C, SINGLE AMINO ACID SUBSTITUTION,
PROTEIN SEQUENCE
MLDSLVSKLPSLSTSDHASVVALN-
LFVALLCACIVLGHLLEENRWMNESI-
TALLIGLGTGVTILLISKGKSSHLLVFSED LFFIYLL-
PPIIFNAGFQVKKKQFFRNFVTIMLFGAVGTIISCTII-
SLGVTQFFKKLDIGTFDLGDYLAIGAIFAATDSVC
TLQVLNQDETPLLYSLVFGEGVVNDATS-
VVVFNAIQSFDLTHLNHEAAFHLLGN-
FLYLFLLSTLLGAATGLISAYVIKKL YFGRHST-
DREVALMMLMAYLSYMLAELFDLSGILTVFFCGI-
VMSHYTWHNVTESSRITTKHTFATLS-
FLAETFIFLYVGM DALDIDKWRSVSDTPGTSIA-
VSSILMGLVMVGRAAFVFPLSFLSN-
LAKKNQSEKINFNMQVVIWWSGLMRGAVSMALA-
YN KFTRAGHTDVRGNAIMITSTITVCLF-
STVVFGMLTKPLISYLLPHQNATTSMLS-
DDNTPKSIHIPLLDQDSFIEPSGNHN VPRPDSIRG-
FLTRPTRTVHYYWRQFDDCFMRPVFGGRGFVPFV-
PGSPTERNPPDLSKA
SEQ ID NO:5

DL-1, 17 amino acids deletion from C-terminus, cDNA
sequence
ATGTTGGATTCTCTAGTGTCGAAACTGC-
CTTCGTTATCGACATCTGATCACGCTTC TGTGGT-
TGCGTTGGAATCTCTTTGTTGCACT-
TCTTTGTGCTTGTATTGTTCTTGGTCA
TCTTTTGGAAGAGAATAGATGGATGAAC-
GAATCCATCACCGCCTTGTTGATTGGG CTAG-
GCACTGGTGTTACCATTTTGTTGATTAG-
TAAAGGAAAAAGCTCGCATCTTC
TCGTCTTTAGTGAAGATCTTTTCT-
TCATATATCTTTTGCCACCCATTATATTCAATG
CAGGGTTTCAAGTAAAAAGAAG-
CAGTTTTTCCGCAATTTCGTGACTATTATGCT
TTTTGGTGCTGTTGGACTATTATTTCT-
TGCACAATCATATCTCAGGTGTAACAC AGT-
TCTTTAAGAAGTTGGACATTGGAAC-
CTTTGACTTGGGTGATTATCTTGCTATT
GGTGCCATATTTGCTGCAACAGATTCAG-
TATGACACTGCAGGTTCTGAATCAAG ACGAGA-
CACCTTTGCTTTACAGTCTTGTATTCG-
GAGAGGGTGTTGTGAATGATGC
AACGCAGTTGTGGTCTTCAACGCGAT-
TCAGAGCTTTGATCTCACTCACCTAAAC CAC-
GAAGCTGCTTTTCATCTTCTTGGAAACT-
TCTTGTATTTGTTTCTCCTAAGTAC
CTTGCTTGGTGCTGCAACCGGTCT-
GATAAGTGCGTATGTTATCAAGAAGCTA
TACTTTGGAAGGCACTCAACTGAC-
CGAGAGGTTGCCCTTATGATGCTTATGGCGT
ATCTTTCTTATATGCTTGCT-
GAGCTTTTCGACTTGAGCGGTATCCT-
CACTGTGTTTT TCTGTGGTATTGTGATGTCCCAT-
TACACATGGCACAATGTAACGGAGAGCTCAAG
AATAACAACAAAGCATACCTTTG-
CAACTTTGTCATTTCTTGCGGAGACATTTATTT
TCTTGTATGTTGGAATGGATGCCTTGGA-
CATTGACAAGTGGAGATCCGTGAGTGA CACAC-
CGGGAACATCGATCGCAGTGAGCT-
CAATCCTAATGGGTCTGGTCATGGTT
GGAAGAGCAGCGTTCGTCTTTCCGT-
TATCGTTTCTATCTAACTTAGCCAAGAAGA
ATCAAAGCGAGAAAATCAACTTTAACAT-
GCAGGTTGTGATTTGGTGGTCTGGTCT CAT-
GAGAGGTGCTGTATCTATGGCTCTTG-
CATACAACAAGTTTACAAGGGCCGGG
CACACAGATGTACGCGGGAATGCAAT-
CATGATCACGAGTACGATAACTGTCTGT CTTTT-
TAGCACAGTGGTGTTTGGTATGCTGAC-
CAAACCACTCATAAGCTACCTATT
ACCGCACCAGAACGCCACCACGAGCAT-
GTTATCTGATGACAACACCCCAAAATC CATA-
CATATCCCTTTGTTGGACCAAGACTCGT-
TCATTGAGCCTTCAGGGAACCAC
AATGTGCCTCGGCCTGACAGTATACGTG-
GCTTCTTGACACGGCCCACTCGAACCG TGCAT-
TACTACTGGAGACAATTTGATGACTCCT-
TCATGCGACCCGTCTTTGGAGG
TCGTGGCTTTGTACCC
SEQ ID NO:6

DL-1, 17 AMINO ACIDS DELETION FROM C-TERMI-
NUS, PROTEIN SEQUENCE
MLDSLVSKLPSLSTSDHASVVALN-
LFVALLCACIVLGHLLEENRWMNESITALLIGLG
TGVTILLISKGKSSHLLVF-
SEDLFFIYLLPPIIFNAGFQVKKKQF-
FRNFVTIMLFGAVGTI ISCTIISLGVTQFFKKLDIGT-
FDLGDYLAIGAIFAATDSVCTLQVLNQDETPLLYS-
LVFG EGVVNDATSVVVFNAIQSFDLTHLN-
HEAAFHLLGNFLYLFLLSTLLGAATGLISAYVI
KKLYFGRHSTDREVALMMLMAYLSYM-
LAELFDLSGILTVFFCGIVMSHYTWHNVTE SSRIT-
TKHTFATLSFLAETFIFLYVGMDALDID-
KWRSVSDTPGTSIAVSSILMGLVMVG
RAAFVFPLSFLSNLAKKNQSEKINFNM-
QVVIWWSGLMRGAVSMALAYNKFTRAGH
TDVRGNAIMITSTITVCLFSTVVFGMLT-
KPLISYLLPHQNATTSMLSDDNTPKSIHIPLL DQDS-
FIEPSGNHNVPRPDSIRGFLTRP-
TRTVHYYWRQFDDSFMRPVFGGRGFVP
SEQ ID NO:7

DL-2, 47 AMINO ACIDS DELETION FROM C-TERMI-
NUS, CDNA SEQUENCE
atgtggattctctagtgtcgaaactgc-
cttcgttatcgacatctgatcacgcttcgtggttgcgtttgaatctctttgt
tgcacttctttgtgcttgtattgttct-
tggtcatcttttggaagagaatagatggatgaacgaatccatcaccgccttgt
tgattgggctaggcactggtgttac-
catttttgttgattagtaaaggaaaaagctcgcatcttctcgtctttagtgaagat
cttttcttcatatatcttttgccac-
ccattatattcaatgcagggtttcaagtaaaaaagaagcagttttccgcaattt
cgtgactattatgcttttggtgctgt-
tgggactattatttcttgcacaatcatatctctaggtgtaacacagttcttta
agaagttggacattggaacctttgacttgggtgattatcttgctattggtgccatatttgctgcaacagattcagtatgtacactgcaggttctgaatcaagacgagacacctttgctttacagtcttgtattcggagagggtgttgtgaatgatgcaacgtcagttgtggtcttcaacgcgattcagagctttgatctcactcacctaaaccacgaagctgcttttcatcttcttggaa acttcttgtatttgtttctcctaagtaccttgcttggtgctgcaaccggtctgataagtgcgtatgttatcaagaagctatactttggaaggcactcaactgaccgagaggttgcccttatgatgcttatgcgtatctttcttatatgcttgctgagcttcgacttgagcggtatcctcactgtgtttttctgtggtattgtgatgtcccattacacatggcacaatgtaacggaga gctcaagaataacaacaaagcatacctttgcaactttgtcatttcttgcggagacatttattttcttgtatgttggaatggatgccttggacattgacaagtggagatccgtgagtgacacaccgggaacatcgatcgcagtgagctcaatcctaatggg tcgggtcatggttggaagagcagcgttcgtcttccgttatcgtttctatctaacttagccaagaagaatcaaagcgaga aaatcaactttaacatgcaggttgtgatttggtggtctggtctcatgagaggtgctgtatctatggctcttgcatacaacaagtttacaagggccgggcacacagatgtacgcgggaatgcaatcatgatcacgagtacgataactgtctgtcttttagcacagtggtgtttggtatgctgaccaaaccactcataagctaccattaccgcacagaacgccaccacgagcatgttat ctgatgacaacaccccaaaatccatacatatcccctttgttggaccaagactcgttcattgagccttcagggaaccacaat gtgcctcggcctgacagtatacgtggcttcttg
SEQ ID NO:8

DL-2, 47 AMINO ACIDS DELETION FROM C-TERMINUS, PROTEIN SEQUENCE
MLDSLVSKLPSLSTSDHASVVALN-LFVALLCACIVLGHLLEENRWMNESITALLIGLG TGVTILLISKGKSSHLLVF-SEDLFFIYLLPPIIFNAGFQVKKKQF-FRNFVTIMLFGAVGTI ISCTIISLGVTQFFKKLDIGT-FDLGDYLAIGAIFAATDSVCTLQVLNQDETPLLYS-LVFG EGVVNDATSVVVFNAIQSFDLTHLN-HEAAFHLLGNFLYLFLLSTLLGAATGLISAYVI KKLYFGRHSTDREVALMMLMAYLSYM-LAELFDLSGILTVFFCGIVMSHYTWHNVTE SSRIT-TKHTFATLSFLAETFIFLYVGMDALDID-KWRSVSDTPGTSIAVSSILMGLVMVG RAAFVFPLSFLSNLAKKNQSEKINFNM-QVVIWWSGLMRGAVSMALAYNKFTRAGH TDVRGNAIMITSTITVCLFSTVVFGMLT-KPLISYLLPHQNATTSMLSDDNTPKSIHIPLL DQDS-FIEPSGNHNVPRPDSIRGFL
SEQ ID NO:9

DL-3, 84 AMINO ACIDS DELETION FROM C-TERMINUS, CDNA SEQUENCE
atgttggattctctagtgtcgaaactgccttcgttatcgacatctgatcacgcttcgtggttgcgttaatctctttgt tgcacttctttgtgcttgtattgttcttggtcatcttttggaagagaatagatggatgaacgaatccatcaccgccttgttgattgggctaggcactggtgttaccattttgttgattagtaaaggaaaaagctcgcatctctcgtctttagtgaagatctttttcttcatatatcttttgccaccccattatattcaatgcagggtttcaagtaaaaaagaagcagttttccgcaatttcgtgactattatgctttttggtgctgtgggactattatttcttgcacaatcatatctctaggtgtaacacagttcttaagaagttggacattggaacctttgacttgggtgattatcttgctattggtgccatatttgctgcaacagattcagtatgtacactgcaggttctgaatcaagacgagacacctttgctttacagtcttgtattcggagagggtgttgtgaatgatgcaacgtcagttgtggtcttcaacgcgattcagagctttgatctcactcacctaaaccacgaagctgcttttcatcttcttggaa acttcttgtatttgtttctcctaagtaccttgcttggtgctgcaaccggtctgataagtgcgtatgttatcaagaagctatactttggaaggcactcaactgaccgagaggttgcccttatgatgcttatgcgtatctttcttatatgcttgctgagcttcgacttgagcggtatcctcactgtgtttttctgtggtattgatgtcccattacacatggcacaatgtaacggaga gctcaagaataacaacaagcatacctttgcaactttgtcatttcttgcggagacatttattttcttgtatgttggaatggatgccttggacattgacaagtggagatccgtgagtgacacaccgggaacatcgatcgcagtgagctcaatcctaatggg tctggtcatggttggaagagcagcgttcgtcttccgttatcgtttctatctaacttagccaagaagaatcaagcgaga aatcaactttaacatgcaggttgtgatttggtggtctggtctcatgagaggtgctgtatctatggctcttgcatacaacaagtttacaagggccgggcacacagatgtacgcgggaatgcaatcatgatcacgagtacgataactgtctgtcttttagcacagtggtgtttggtatgctgaccaaaccactcataagctaccattaccgcaccagaacgccaccacgagcatgttat ct
SEQ ID NO:10

DL-3, 84 AMINO ACIDS DELETION FROM C-TERMINUS, PROTEIN SEQUENCE
MLDSLVSKLPSLSTSDHASVVALN-LFVALLCACIVLGHLLEENRWMNESITALLIGLG TGVTILLISKGKSSHLLVF-SEDLFFIYLLPPIIFNAGFQVKKKQF-FRNFVTIMLFGAVGTI ISCTIISLGVTQFFKKLDIGT-FDLGDYLAIGAIFAATDSVCTLQVLNQDETPLLYS-LVFG EGVVNDATSVVVFNAIQSFDLTHLN-HEAAFHLLGNFLYLFLLSTLLGAATGLISAYVI KKLYFGRHSTDREVALMMLMAYLSYM-LAELFDLSGILTVFFCGIVMSHYTWHNVTE SSRIT-TKHTFATLSFLAETFIFLYVGMDALDID-KWRSVSDTPGTSIAVSSILMGLVMVG RAAFVFPLSFLSNLAKKNQSEKINFNM-WVVIWWSGLMRGAVSMALAYNKFTRAGH TDVRGNAIMITSTITVCLFSTVVFGMLT-KPLISYLLPHQNATTSMLS
SEQ ID NO:11

NDL-1 cDNA sequence
atggcttctgtggttgcgtgaatctcttgttgcacttctttgtgcttgtattgttcttggtcatcttttggaagagaatagatggatgaacgaatccatcaccgccttgttgattgggctaggcactggtgttaccattttgttgattagtaaaggaaaaagctcgcatcttctcgtctttagtgaagatctttttcttcatatatcttttgccacccattatattcaatgcagggttt caagtaaaaaagaagcagttttccgcaatttcgtgactattatgctttttggtgctgttgggactattatttcttgcacaatcatatctctaggtgtaacacagttctttaagaagttggacattggaacctttgacttgggtgattatcttgctattggtgccatatttgctgcaacagattcagtatgtacactgcaggttctgaatcaagacgagacacctttgctttacagtcttgtattcggagagggtgttgtgaatgatgcaacgtcagttgtggtcttcaacgcgattcagagctttgatctcactcaccctaaaccacgaagctgcttttcatcttcttggaaacttcttgtatttgtttctcctaagtaccttgcttggtgctgcaaccg gtcgataagtgcgtatgttatcaagaagctatactttggaaggcactcaactgaccgagaggttgcccttatgatgcttatgcgtatctttcttatatgcttgctgagcttttggacttgagcggtatcctcactgtgtttttctgtggtattgtgat gtcccattacacatggcacaatgtaacgagagctcaagaataacaacaaagcatacctttgcaactttgtcatttcttg cggagacatttattttcttgtatgttgaatggatgccttggacattgacaagtggagatccgtgagtgacacaccggga acatcgatcgcagtgagctcaatctaatgggtctggtcatggttggaagagcagcgttcgtcttccgttatcgtttct atctaacttagccaagaagaatcaaagc gagaaaatcaactttaacatgcaggttgtgatttggtggtctggtctcatga gaggtgctgtatctatggctcttgcatacaacaagtttacaagggccgggcacacagatgtacgcgggaatgcaatcatgatcacgagtacgataactgtctgtcttttagcacagtggtgtttggtatgctgaccaaaccactcataagctacctatt accgcaccagaacgccaccacgagcatgttatctgatgacaacacccaaaatccatacatatcccttgttggaccaag actcgttcattgagccttcagggaaccacaatgtgcctcggcctgacagtatacgtggcttcttgacacggcccactcgaaccgtgcattactactggagacaatttgatgactcctcatgcgaccgtctttggaggtcgtggctttgtaccctttgt tccaggttctccaactgagagaaaccctcctgatcttagtaaggct
SEQ ID NO:12

NDL-1 protein sequence
MASVVALNLFVALLCACIVLGHLLEENR-WMNESITALLIGLGTGVTILLISKGKSSHL LVFSEDDLFFIYLLPPIIFNAGFQVKKKQFFRN-FVTIMLFGAVGTIISCTIISLGVTQFFKKLDIGTFDLGDYLAIGAIFAATDS-VCTLQVLNQDETPLLYSLVFGEGVVNDATSVVVFNAIQSFDLTHLNHEAAFHLLGNFLY-LFLLSTLLGAATGLISAYVIKKLYFGRHSTDREVALMMLMAYLSYMLAELFDLS-GILTVFFCGIVMSHYTWHNVTESSRITTKHTFATLSFLAETFIFLYVGMDALDIDKWRSVSDT-PGTSIAVSSILMGLVMVGRAAFVFPLSFLSNLAKKNQSEKINFNMQVVIWWSGLMR-GAVSMALAYNKFTRAGHTDVRGNAIMITSTITVCLFSTVVFGMLTKPLISYLL-PHQNATTSMLSDDNTPKSIHIPLLDQDS-FIEPSGNHN VPRPDSIRGFLTRPTRTVHYYWRQFDDSFMRPVFGGRGFVPFVPGSPTERNPPDLSKA
SEQ ID NO:13

NDL-2 cDNA sequence
atgaaaagctcgcatcttctcgtcttagtgaagatcttttcttcatatatctttgccaccattataucaatgcagggtttcaagtaaaaagaagcagttttccgcaatttcgtgactattatgcttttggtgctgttgggactattattjctt gcacaatcatatctctaggtgtaacacagttctttaagaagttggacattggaacctttgacttgggtgattatcttgctattggtgccatatttgctgcaacagattcagtatgtacactgcaggttctgaatcaagacgagacacctttgctttacagtcttgtattcggagagggtgttgtgaatgatgcaacgtcagttgtggtcttcaacgcgattcagagctttgatctcactcacctaaaccacgaagctgcttttcatcttcttggaaacttcttgtatttgtttctcctaagtaccttgcttggtgctgca accggtctgataagtgcgtatgttatcaagaagctatactttggaaggcactcaactgaccgagaggttgcccttatgatgcttatggcgtatctttcttatatgcttgctgagcttttcgacttgagcggtatcctcactgtgtuttctgtggtattg tgatgtcccattacacatggcacaatgtaacgagagctcaagaataacaacaaagcataccttgcaactttgtcatttcttgcggagacatttattttcttgtattgttggaatggatgccttggacattgacaagtggagatccgtgagtgacacacccgggaacatcgatcgcagtgagctcaatcctaatgggtctggtcatggttggaagagcagcgttcgtcttttccgttatcgt ttctatctaacttagccaagaagaatcaaagcgagaaaatcaactttaacatgcaggttgtgatttggtggtctggtctcatgagaggtgctgtatctatggctcttgcatacaacaagtttacaagggccgggcacacagatgtacgcgggaatgcaatcatgatcacgagtacgataactgtctgtcttttagcacagtggtgtttggtatgctgaccaaaccactcataagctacctatt accgcaccagaacgccaccacgagcatgttatctgatgacaacacccaaaatccatacatatcccttgttggac caagactcgttcattgagccttcagggaaccacaatgtgcctcggcctgacagtatacgtggcttcttgacacggcccactcgaaccgtgcattactactggagacaatttgatgactcctcatgcgacccgtctttggaggtcgtggctttgtacccttgttcc aggttctccaactgagagaaaccctcctgatcttagtaaggct
SEQ ID NO:14

NDL-2 protein sequence
MKSSHLLVFSEDLFFIYLLPPIIFNAG-FQVKKKQFFRNFVTIMLFGAVGTIISCTIISLGV TQFFKKLDIGTFDLGDY-LAIGAIFAATDSVCTLQVLNQDET-PLLYSLVFGEGVVNDAT SVVVFNAIQSFDLTHLN-HEAAFHLLGNFLYLFLLSTLLGAATGLISAYVIKK-LYFGRH STDREVALMMLMAYLSYMLAELFDLS-GILTVFFCGIVMSHYTWHNVTESSRITTKHT FATLSFLAETFIFLYVGMDALDIDKWRS-VSDTPGTSIAVSSILMGLVMVGRAAFVFPL SFLSN-LAKKNQSEKINFNMQVVIWWSGLMR-GAVSMALAYNKFTRAGHTDVRGNAI MITSTITVCLFSTVVFGMLTKPLISYLL-PHQNATTSMLSDDNTPKSIHIPLLDQDSFIEPS GNHNVPRPDSIRGFLTRPTRTVHYY-WRQFDDSFMRPVFGGRGFVPFVPGSPTERNPP DLSKA
SEQ ID NO:15

NDL-3 cDNA sequence
atgaaaagaagcagttttccgcaatttcgtgactattatgcttttggtgctgttgggactattatttcttgcacaatcatatctctaggtgtaacacagttcttताagaagttggacattggaaccttigacttgggtgattatcttgctattggtgccatatttgctgcaacagattcagtatgtacactgcaggttctgaatcaagacgagacacctttgctttacagtcttgta ttcggagagggtgttgtgaatgatgcaacgtcagttgtggtcttcaacgcgattcagagctttgatctcactcacctaaaccacgaagctgcttttcatcttcttggaaacttcttgtatttgtttctcctaagtaccttgcttggtgctgcaaccggtctgataagtgcgtatgttatcaagaagctatactttggaaggcactcaactgaccgagaggttgcccttatgatgcttatggcgtatctttcttatatgcttgctgagcttttcgacttgagcggtatcctcactgtgtttttctgtggtattgtgatgtcccattacacatggcacaatgtaacgagagctcaagaataacaacaaagcataccttgcaactttgtcatttcttgcggagacattcttgtatgttggaatggatgccttggacattgacaagtggagatccgtgagtgacacaccgggaacatcgatcgcagtgagctcaatctaatgggtctggtcatggttggaagagcagcgttcgtcttccgttatcgttctatc taacttagccaagaagaatcaaagcgagaaaatcaactttaacatgcaggttgtgatttggtggtctggtctcatgagaggtgctgtatctatggctcttgcatacaacaagtttacaagggccgggcacacagatgtacgcgggaatgcaatcatgatcacgagtacgataactgtctgtctttttagcacagtggtgtttggtatgctgaccaaaccactcataagctacctattaccgcaccagaacgccaccacgagcatgttatctgatgacaacacccaaaatccatacatatcccttgttggaccaagactcgttcattgagccttcagggaaccacaatgtgcctcggcctgacagtatacgtggcttcttgacacggcccactcgaacc gtgcattactactggagacaatttgatgactcctcatgcgacccgtctttggaggtcgtggctttgtacccttt-gttcc aggttctccaactgagagaaaccctcctgatcttagtaaggct
SEQ ID NO:16

NDL-3 protein sequence
MKKKQFFRNFVTIMLFGAVGTIISCTI-ISLGVTQFFKKLDIGTFDLGDYLAIGAIFAATD SVCTLQVLNQDETPLLYSLVFGEGVVN-DATSVVVFNAIQSFDLTHLNHEAAFHLLGN FLY- LFLLSTLLGAATGLISAYVIKKLYF-
GRHSTDREVALMMLMAYLSYMLAELFDLS
GILTVFFCGIVMSHYTWHNVTESSRITT-
KHTFATLSFLAETFIFLYVGMDALDIDKWR SVSDT-
PGTSIAVSSILMGLVMVGRAAFVFPLS-
FLSNLAKKNQSEKINFNMQVVIWWS GLMRGAVSMALAYNKFTRAGHTDVRG-
NAIMITSTITVCLFSTVVFGMLTKPLISYLL
PHQNATTSMLSDDNTPKSIHIPLLDQDS-
FIEPSGNHNVPRPDSIRGFLTRPTRTVHYYW
RQFDDSFMRPVFGGRGFVPFVPG-
SPTERNPPDLSKA

---

What is claimed is:

1. A recombinant DNA vector comprising a promoter operably linked to a heterologous truncated NHX1 polynucleotide sequence which consists of a coding sequence encoding a C-terminally truncated NHX1 polypeptide which has at least 95% sequence identity to SEQ ID NO:2, wherein said truncated NHX1 polypeptide has 17 to 84 C-terminal acids deleted, and wherein the truncated NHX1 polypeptide confers increased Na+ tolerance in a plant compared to a plant into which the truncated NHX1 polynucleotide was not introduced.

2. The recombinant DNA vector of claim 1, wherein the truncated NHX1 polynucleotide sequence is SEQ ID NO. 9.

3. The recombinant DNA vector of claim 1, wherein the truncated NHX1 polypeptide sequence is SEQ ID NO: 10.

4. The recombinant DNA vector of claim 1, wherein the truncated NHX1 polypeptide is less than 500 amino acids in length.

5. The recombinant DNA vector of claim 1, wherein the truncated NHX1 polypeptide is less than 475 amino acids in length.

6. The recombinant DNA vector of claim 1, wherein the promoter is a plant promoter.

7. A purified truncated NHX1 polynucleotide encoding a C-terminally truncated NHX1 polypeptide which has at least 95% sequence identity to SEQ ID NO:2, wherein said truncated NHX1 polypeptide has 17 to 84 C-terminal acids deleted, and wherein the truncated NHX1 polypeptide confers increased Na+ tolerance in a plant compared to a plant into which truncated NHX1 polynucleotide was not introduced.

8. The purified NHX1 polynucleotide of claim 7, wherein the truncated NHX1 polynucleotide sequence is SEQ ID NO. 9.

9. The purified NHX1 polynucleotide of claim 7, wherein the truncated NHX1 polypeptide is SEQ ID NO: 10.

10. The purified NHX1 polynucleotide of claim 7, wherein the truncated NHX1 polypeptide is less than 500 amino acids in length.

11. The purified NHX1 polynucleotide of claim 7, wherein the truncated NHX1 polypeptide is less than 475 amino acids in length.

* * * * *

SEQUENCE LISTING

<160> NUMBER OF SEQ ID NOS: 22

<210> SEQ ID NO 1
<211> LENGTH: 1614
<212> TYPE: DNA
<213> ORGANISM: Arabidopsis thaliana

<400> SEQUENCE: 1

```
atgttggatt ctctagtgtc gaaactgcct tcgttatcga catctgatca cgcttctgtg     60
gttgcgttga atctctttgt tgcacttctt tgtgcttgta ttgttcttgg tcatcttttg    120
gaagagaata gatggatgaa cgaatccatc accgccttgt tgattgggct aggcactggt    180
gttaccattt tgttgattag taaaggaaaa agctcgcatc ttctcgtctt tagtgaagat    240
ctttctctca tatatctttt gccacccatt atattcaatg cagggtttca agtaaaaaag    300
aagcagtttt tccgcaattt cgtgactatt atgcttttg tgctgttgg gactattatt    360 tcttgcacaa tcatatctct aggtgtaaca cagttcttta agaagttgga cattggaacc    420
tttgacttgg gtgattatct tgctattggt gccatatttg ctgcaacaga ttcagtatgt    480
acactgcagg ttctgaatca agacgagaca cctttgcttt acagtcttgt attcggagag    540
ggtgttgtga atgatgcaac gtcagttgtg gtcttcaacg cgattcagag ctttgatctc    600
actcacctaa accacgaagc tgcttttcat cttcttggaa acttcttgta tttgtttctc    660
ctaagtacct tgcttggtgc tgcaaccggt ctgataagtg cgtatgttat caagaagcta    720
tactttggaa ggcactcaac tgaccgagag gttgcccta tgatgcttat ggcgtatctt    780
tcttatatgc ttgctgagct tttcgacttg agcggtatcc tcactgtgtt tttctgtggt    840
attgtgatgt cccattacac atggcacaat gtaacggaga gctcaagaat aacaacaaag    900
catacctttg caactttgtc atttcttgcg gagacattta ttttcttgta tgttggaatg    960
gatgccttgg acattgacaa gtggagatcc gtgagtgaca caccgggaac atcgatcgca   1020
gtgagctcaa tcctaatggg tctggtcatg gttggaagag cagcgttcgt ctttccgtta   1080
tcgtttctat ctaacttagc caagaagaat caaagcgaga aaatcaactt taacatgcag   1140
gttgtgattt ggtggtctgg tctcatgaga ggtgctgtat ctatggctct tgcatacaac   1200
aagtttacaa gggccgggca cacagatgta cgcgggaatg caatcatgat cacgagtacg   1260
ataactgtct gtcttttag cacagtggtg tttggtatgc tgaccaaacc actcataagc   1320
tacctattac cgcaccagaa cgccaccacg agcatgttat ctgatgacaa cccccaaaa   1380 tccatacata tcccttttgtt ggaccaagac tcgttcattg agccttcagg gaaccacaat   1440
gtgcctcggc ctgacagtat acgtggcttc ttgacacggc ccactcgaac cgtgcattac   1500
tactggagac aatttgatga ctccttcatg cgacccgtct tggaggtcg tggctttgta   1560 ccctttgttc caggttctcc aactgagaga aaccctcctg atcttagtaa ggct         1614
```

<210> SEQ ID NO 2
<211> LENGTH: 538
<212> TYPE: PRT

<213> ORGANISM: Arabidopsis thaliana

<400> SEQUENCE: 2

```
Met Leu Asp Ser Leu Val Ser Lys Leu Pro Ser Leu Ser Thr Ser Asp
1               5                   10                  15

His Ala Ser Val Val Ala Leu Asn Leu Phe Val Ala Leu Leu Cys Ala
                20                  25                  30

Cys Ile Val Leu Gly His Leu Leu Glu Glu Asn Arg Trp Met Asn Glu
            35                  40                  45

Ser Ile Thr Ala Leu Leu Ile Gly Leu Gly Thr Gly Val Thr Ile Leu
        50                  55                  60

Leu Ile Ser Lys Gly Lys Ser Ser His Leu Leu Val Phe Ser Glu Asp
65                  70                  75                  80

Leu Phe Phe Ile Tyr Leu Leu Pro Pro Ile Ile Phe Asn Ala Gly Phe
                85                  90                  95

Gln Val Lys Lys Lys Gln Phe Phe Arg Asn Phe Val Thr Ile Met Leu
                100                 105                 110

Phe Gly Ala Val Gly Thr Ile Ile Ser Cys Thr Ile Ile Ser Leu Gly
            115                 120                 125

Val Thr Gln Phe Phe Lys Lys Leu Asp Ile Gly Thr Phe Asp Leu Gly
        130                 135                 140

Asp Tyr Leu Ala Ile Gly Ala Ile Phe Ala Ala Thr Asp Ser Val Cys
145                 150                 155                 160

Thr Leu Gln Val Leu Asn Gln Asp Glu Thr Pro Leu Leu Tyr Ser Leu
                165                 170                 175

Val Phe Gly Glu Gly Val Val Asn Asp Ala Thr Ser Val Val Val Phe
                180                 185                 190

Asn Ala Ile Gln Ser Phe Asp Leu Thr His Leu Asn His Glu Ala Ala
            195                 200                 205

Phe His Leu Leu Gly Asn Phe Leu Tyr Leu Phe Leu Leu Ser Thr Leu
        210                 215                 220

Leu Gly Ala Ala Thr Gly Leu Ile Ser Ala Tyr Val Ile Lys Lys Leu
225                 230                 235                 240

Tyr Phe Gly Arg His Ser Thr Asp Arg Glu Val Ala Leu Met Met Leu
                245                 250                 255

Met Ala Tyr Leu Ser Tyr Met Leu Ala Glu Leu Phe Asp Leu Ser Gly
                260                 265                 270

Ile Leu Thr Val Phe Phe Cys Gly Ile Val Met Ser His Tyr Thr Trp
            275                 280                 285

His Asn Val Thr Glu Ser Ser Arg Ile Thr Thr Lys His Thr Phe Ala
        290                 295                 300

Thr Leu Ser Phe Leu Ala Glu Thr Phe Ile Phe Leu Tyr Val Gly Met
305                 310                 315                 320

Asp Ala Leu Asp Ile Asp Lys Trp Arg Ser Val Ser Asp Thr Pro Gly
                325                 330                 335

Thr Ser Ile Ala Val Ser Ser Ile Leu Met Gly Leu Val Met Val Gly
            340                 345                 350

Arg Ala Ala Phe Val Phe Pro Leu Ser Phe Leu Ser Asn Leu Ala Lys
        355                 360                 365

Lys Asn Gln Ser Glu Lys Ile Asn Phe Asn Met Gln Val Val Ile Trp
370                 375                 380

Trp Ser Gly Leu Met Arg Gly Ala Val Ser Met Ala Leu Ala Tyr Asn
                390                 395                 400
```
385

```
Lys Phe Thr Arg Ala Gly His Thr Asp Val Arg Gly Asn Ala Ile Met
                405                 410                 415
Ile Thr Ser Thr Ile Thr Val Cys Leu Phe Ser Thr Val Phe Gly
            420                 425                 430
Met Leu Thr Lys Pro Leu Ile Ser Tyr Leu Leu Pro His Gln Asn Ala
            435                 440                 445
Thr Thr Ser Met Leu Ser Asp Asp Asn Thr Pro Lys Ser Ile His Ile
            450                 455                 460
Pro Leu Leu Asp Gln Asp Ser Phe Ile Glu Pro Ser Gly Asn His Asn
465                 470                 475                 480
Val Pro Arg Pro Asp Ser Ile Arg Gly Phe Leu Thr Arg Pro Thr Arg
                485                 490                 495
Thr Val His Tyr Tyr Trp Arg Gln Phe Asp Asp Ser Phe Met Arg Pro
                500                 505                 510
Val Phe Gly Gly Arg Gly Phe Val Pro Phe Val Pro Gly Ser Pro Thr
            515                 520                 525
Glu Arg Asn Pro Pro Asp Leu Ser Lys Ala
530                 535

<210> SEQ ID NO 3
<211> LENGTH: 1614
<212> TYPE: DNA
<213> ORGANISM: Artificial
<220> FEATURE:
<223> OTHER INFORMATION: Modified AtNHX1 SM-23

<400> SEQUENCE: 3
atgttggatt ctctagtgtc gaaactgcct tcgttatcga catctgatca cgcttctgtg      60
gttgcgttga atctctttgt tgcacttctt tgtgcttgta ttgttcttgg tcatcttttg     120
gaagagaata gatggatgaa cgaatccatc accgccttgt tgattgggct aggcactggt     180
gttaccattt tgttgattag taaaggaaaa agctcgcatc ttctcgtctt tagtgaagat     240
cttttcttca tatatctttt gccacccatt atattcaatg cagggtttca agtaaaaaag     300
aagcagtttt ccgcaatttt cgtgactatt atgctttttg gtgctgttgg gactattatt     360
tcttgcacaa tcatatctct aggtgtaaca cagttcttta agaagttgga cattggaacc     420
tttgacttgg gtgattatct tgctattggt gccatatttg ctgcaacaga ttcagtatgt     480
acactgcagg ttctgaatca agacgagaca cctttgcttt acagtcttgt attcggagag     540
ggtgttgtga atgatgcaac gtcagttgtg gtcttcaacg cgattcagag ctttgatctc     600
actcacctaa accacgaagc tgcttttcat cttcttggaa acttcttgta tttgtttctc     660
ctaagtacct tgcttggtgc tgcaaccggt ctgataagtg cgtatgttat caagaagcta     720
tactttggaa ggcactcaac tgaccgagag gttgcccctta tgatgcttat ggcgtatctt     780
tcttatatgc ttgctgagct tttcgacttg agcggtatcc tcactgtgtt tttctgtggt     840
attgtgatgt cccattacac atggcacaat gtaacggaga gctcaagaat aacaacaaag     900
cataccttg caactttgtc atttcttgcg gagacatttt tttcttgta tgttggaatg     960
gatgccttgg acattgacaa gtggagatcc gtgagtgaca caccgggaac atcgatcgca    1020
gtgagctcaa tcctaatggg tctggtcatg gttggaagag cagcgttcgt ctttccgtta    1080
tcgtttctat ctaacttagc caagaagaat caaagcgaga aaatcaactt taacatgcag    1140
gttgtgattt ggtggtctgg tctcatgaga ggtgctgtat ctatggctct tgcatacaac    1200
aagtttacaa gggccgggca cacagatgta cgcgggaatg caatcatgat cacgagtacg    1260
```

-continued

```
ataactgtct gtcttttag cacagtggtg tttggtatgc tgaccaaacc actcataagc    1320
tacctattac cgcaccagaa cgccaccacg agcatgttat ctgatgacaa caccccaaaa    1380
tccatacata tccctttgtt ggaccaagac tcgttcattg agccttcagg gaaccacaat    1440
gtgcctcggc ctgacagtat acgtggcttc ttgacacggc ccactcgaac cgtgcattac    1500
tactggagac aatttgatga ctgcttcatg cgacccgtct ttggaggtcg tggctttgta    1560 cccttgttc caggttctcc aactgagaga aaccctcctg atcttagtaa ggct           1614
```

<210> SEQ ID NO 4
<211> LENGTH: 538
<212> TYPE: PRT
<213> ORGANISM: Artificial
<220> FEATURE:
<223> OTHER INFORMATION: Putative amino acid sequence encoded by modified AtNHX1 SM-23

<400> SEQUENCE: 4

```
Met Leu Asp Ser Leu Val Ser Lys Leu Pro Ser Leu Ser Thr Ser Asp
1               5                   10                  15

His Ala Ser Val Val Ala Leu Asn Leu Phe Val Ala Leu Leu Cys Ala
            20                  25                  30

Cys Ile Val Leu Gly His Leu Leu Glu Glu Asn Arg Trp Met Asn Glu
        35                  40                  45

Ser Ile Thr Ala Leu Leu Ile Gly Leu Gly Thr Gly Val Thr Ile Leu
    50                  55                  60

Leu Ile Ser Lys Gly Lys Ser Ser His Leu Leu Val Phe Ser Glu Asp
65                  70                  75                  80

Leu Phe Phe Ile Tyr Leu Leu Pro Pro Ile Ile Phe Asn Ala Gly Phe
                85                  90                  95

Gln Val Lys Lys Lys Gln Phe Phe Arg Asn Phe Val Thr Ile Met Leu
            100                 105                 110

Phe Gly Ala Val Gly Thr Ile Ile Ser Cys Thr Ile Ile Ser Leu Gly
        115                 120                 125

Val Thr Gln Phe Phe Lys Lys Leu Asp Ile Gly Thr Phe Asp Leu Gly
    130                 135                 140

Asp Tyr Leu Ala Ile Gly Ala Ile Phe Ala Ala Thr Asp Ser Val Cys
145                 150                 155                 160

Thr Leu Gln Val Leu Asn Gln Asp Glu Thr Pro Leu Leu Tyr Ser Leu
                165                 170                 175

Val Phe Gly Glu Gly Val Val Asn Asp Ala Thr Ser Val Val Val Phe
            180                 185                 190

Asn Ala Ile Gln Ser Phe Asp Leu Thr His Leu Asn His Glu Ala Ala
        195                 200                 205

Phe His Leu Leu Gly Asn Phe Leu Tyr Leu Phe Leu Leu Ser Thr Leu
    210                 215                 220

Leu Gly Ala Ala Thr Gly Leu Ile Ser Ala Tyr Val Ile Lys Lys Leu
225                 230                 235                 240

Tyr Phe Gly Arg His Ser Thr Asp Arg Glu Val Ala Leu Met Met Leu
                245                 250                 255

Met Ala Tyr Leu Ser Tyr Met Leu Ala Glu Leu Phe Asp Leu Ser Gly
            260                 265                 270

Ile Leu Thr Val Phe Phe Cys Gly Ile Val Met Ser His Tyr Thr Trp
        275                 280                 285

His Asn Val Thr Glu Ser Ser Arg Ile Thr Thr Lys His Thr Phe Ala
    290                 295                 300
```

```
Thr Leu Ser Phe Leu Ala Glu Thr Phe Ile Phe Leu Tyr Val Gly Met
305                 310                 315                 320

Asp Ala Leu Asp Ile Asp Lys Trp Arg Ser Val Ser Asp Thr Pro Gly
            325                 330                 335

Thr Ser Ile Ala Val Ser Ser Ile Leu Met Gly Leu Val Met Val Gly
                340                 345                 350

Arg Ala Ala Phe Val Phe Pro Leu Ser Phe Leu Ser Asn Leu Ala Lys
            355                 360                 365

Lys Asn Gln Ser Glu Lys Ile Asn Phe Asn Met Gln Val Val Ile Trp
    370                 375                 380

Trp Ser Gly Leu Met Arg Gly Ala Val Ser Met Ala Leu Ala Tyr Asn
385                 390                 395                 400

Lys Phe Thr Arg Ala Gly His Thr Asp Val Arg Gly Asn Ala Ile Met
                405                 410                 415

Ile Thr Ser Thr Ile Thr Val Cys Leu Phe Ser Thr Val Phe Gly
                420                 425                 430

Met Leu Thr Lys Pro Leu Ile Ser Tyr Leu Leu Pro His Gln Asn Ala
            435                 440                 445

Thr Thr Ser Met Leu Ser Asp Asp Asn Thr Pro Lys Ser Ile His Ile
    450                 455                 460

Pro Leu Leu Asp Gln Asp Ser Phe Ile Glu Pro Ser Gly Asn His Asn
465                 470                 475                 480

Val Pro Arg Pro Asp Ser Ile Arg Gly Phe Leu Thr Arg Pro Thr Arg
                485                 490                 495

Thr Val His Tyr Tyr Trp Arg Gln Phe Asp Asp Cys Phe Met Arg Pro
            500                 505                 510

Val Phe Gly Gly Arg Gly Phe Val Pro Phe Val Pro Gly Ser Pro Thr
        515                 520                 525

Glu Arg Asn Pro Pro Asp Leu Ser Lys Ala
    530                 535

<210> SEQ ID NO 5
<211> LENGTH: 1563
<212> TYPE: DNA
<213> ORGANISM: Artificial
<220> FEATURE:
<223> OTHER INFORMATION: Modified AtNHX1 DL-1

<400> SEQUENCE: 5
atgttggatt ctctagtgtc gaaactgcct tcgttatcga catctgatca cgcttctgtg      60
gttgcgttga atctctttgt tgcacttctt tgtgcttgta ttgttcttgg tcatcttttg     120
gaagagaata gatggatgaa cgaatccatc accgccttgt tgattgggct aggcactggt     180
gttaccattt tgttgattag taaggaaaaa agctcgcatc ttctcgtctt tagtgaagat     240
cttttcttca tatatctttt gccacccatt atattcaatg cagggtttca gtaaaaaag     300 aagcagtttt ccgcaattt cgtgactatt atgcttttg gtgctgttgg gactattatt     360
tcttgcacaa tcatatctct aggtgtaaca cagttcttta agaagttgga cattggaacc     420
tttgacttgg gtgattatct tgctattggt gccatatttg ctgcaacaga ttcagtatgt     480
acactgcagg ttctgaatca agacgagaca cctttgcttt acagtcttgt attcggagag     540
ggtgttgtga atgatgcaac gtcagttgtg gtcttcaacg cgattcagag ctttgatctc     600
actcacctaa accacgaagc tgcttttcat cttcttggaa acttcttgta tttgtttctc     660
ctaagtaccc tgcttggtgc tgcaaccggt ctgataagtg cgtatgttat caagaagcta     720
```

```
tactttggaa ggcactcaac tgaccgagag gttgcccttc tgatgcttat ggcgtatctt    780
tcttatatgc ttgctgagct tttcgacttg agcggtatcc tcactgtgtt tttctgtggt    840
attgtgatgt cccattacac atggcacaat gtaacggaga gctcaagaat aacaacaaag    900 cataccttttg caactttgtc atttcttgcg gagacattta ttttcttgta tgttggaatg    960
gatgccttgg acattgacaa gtggagatcc gtgagtgaca caccgggaac atcgatcgca   1020
gtgagctcaa tcctaatggg tctggtcatg gttggaagag cagcgttcgt ctttccgtta   1080
tcgtttctat ctaacttagc caagaagaat caaagcgaga aaatcaactt taacatgcag   1140
gttgtgattt ggtggtctgg tctcatgaga ggtgctgtat ctatggctct tgcatacaac   1200
aagtttacaa gggccgggca cacagatgta cgcgggaatg caatcatgat cacgagtacg   1260
ataactgtct gtctttttag cacagtggtg tttggtatgc tgaccaaacc actcataagc   1320
tacctattac cgcaccagaa cgccaccacg agcatgttat ctgatgacaa cacccccaaaa   1380 tccatacata tccctttgtt ggaccaagac tcgttcattg agccttcagg gaaccacaat   1440
gtgcctcggc ctgacagtat acgtggcttc ttgacacggc ccactcgaac cgtgcattac   1500
tactggagac aatttgatga ctccttcatg cgacccgtct ttggaggtcg tggctttgta   1560
ccc                                                                 1563
```

<210> SEQ ID NO 6
<211> LENGTH: 521
<212> TYPE: PRT
<213> ORGANISM: Artificial
<220> FEATURE:
<223> OTHER INFORMATION: Putative amino acid sequence encded by modified
      AtNHX1 DL-1

<400> SEQUENCE: 6

```
Met Leu Asp Ser Leu Val Ser Lys Leu Pro Ser Leu Ser Thr Ser Asp
1               5                   10                  15

His Ala Ser Val Val Ala Leu Asn Leu Phe Val Ala Leu Leu Cys Ala
            20                  25                  30

Cys Ile Val Leu Gly His Leu Leu Glu Glu Asn Arg Trp Met Asn Glu
        35                  40                  45

Ser Ile Thr Ala Leu Leu Ile Gly Leu Gly Thr Gly Val Thr Ile Leu
    50                  55                  60

Leu Ile Ser Lys Gly Lys Ser Ser His Leu Leu Val Phe Ser Glu Asp
65                  70                  75                  80

Leu Phe Phe Ile Tyr Leu Leu Pro Pro Ile Ile Phe Asn Ala Gly Phe
                85                  90                  95

Gln Val Lys Lys Lys Gln Phe Phe Arg Asn Phe Val Thr Ile Met Leu
            100                 105                 110

Phe Gly Ala Val Gly Thr Ile Ile Ser Cys Thr Ile Ile Ser Leu Gly
        115                 120                 125

Val Thr Gln Phe Phe Lys Lys Leu Asp Ile Gly Thr Phe Asp Leu Gly
    130                 135                 140

Asp Tyr Leu Ala Ile Gly Ala Ile Phe Ala Ala Thr Asp Ser Val Cys
145                 150                 155                 160

Thr Leu Gln Val Leu Asn Gln Asp Glu Thr Pro Leu Leu Tyr Ser Leu
                165                 170                 175

Val Phe Gly Glu Gly Val Val Asn Asp Ala Thr Ser Val Val Val Phe
            180                 185                 190

Asn Ala Ile Gln Ser Phe Asp Leu Thr His Leu Asn His Glu Ala Ala
```

```
                195                 200                 205
Phe His Leu Leu Gly Asn Phe Leu Tyr Leu Phe Leu Leu Ser Thr Leu
    210                 215                 220

Leu Gly Ala Ala Thr Gly Leu Ile Ser Ala Tyr Val Ile Lys Lys Leu
225                 230                 235                 240

Tyr Phe Gly Arg His Ser Thr Asp Arg Glu Val Ala Leu Met Met Leu
                245                 250                 255

Met Ala Tyr Leu Ser Tyr Met Leu Ala Glu Leu Phe Asp Leu Ser Gly
            260                 265                 270

Ile Leu Thr Val Phe Phe Cys Gly Ile Val Met Ser His Tyr Thr Trp
        275                 280                 285

His Asn Val Thr Glu Ser Ser Arg Ile Thr Thr Lys His Thr Phe Ala
    290                 295                 300

Thr Leu Ser Phe Leu Ala Glu Thr Phe Ile Phe Leu Tyr Val Gly Met
305                 310                 315                 320

Asp Ala Leu Asp Ile Asp Lys Trp Arg Ser Val Ser Asp Thr Pro Gly
                325                 330                 335

Thr Ser Ile Ala Val Ser Ser Ile Leu Met Gly Leu Val Met Val Gly
            340                 345                 350

Arg Ala Ala Phe Val Phe Pro Leu Ser Phe Leu Ser Asn Leu Ala Lys
        355                 360                 365

Lys Asn Gln Ser Glu Lys Ile Asn Phe Asn Met Gln Val Val Ile Trp
    370                 375                 380

Trp Ser Gly Leu Met Arg Gly Ala Val Ser Met Ala Leu Ala Tyr Asn
385                 390                 395                 400

Lys Phe Thr Arg Ala Gly His Thr Asp Val Arg Gly Asn Ala Ile Met
                405                 410                 415

Ile Thr Ser Thr Ile Thr Val Cys Leu Phe Ser Thr Val Phe Gly
            420                 425                 430

Met Leu Thr Lys Pro Leu Ile Ser Tyr Leu Leu Pro His Gln Asn Ala
        435                 440                 445

Thr Thr Ser Met Leu Ser Asp Asp Asn Thr Pro Lys Ser Ile His Ile
    450                 455                 460

Pro Leu Leu Asp Gln Asp Ser Phe Ile Glu Pro Ser Gly Asn His Asn
465                 470                 475                 480

Val Pro Arg Pro Asp Ser Ile Arg Gly Phe Leu Thr Arg Pro Thr Arg
                485                 490                 495

Thr Val His Tyr Tyr Trp Arg Gln Phe Asp Asp Ser Phe Met Arg Pro
            500                 505                 510

Val Phe Gly Gly Arg Gly Phe Val Pro
        515                 520

<210> SEQ ID NO 7
<211> LENGTH: 1473
<212> TYPE: DNA
<213> ORGANISM: Artificial
<220> FEATURE:
<223> OTHER INFORMATION: Modified AtNHX1 DL-2.

<400> SEQUENCE: 7
atgttggatt ctctagtgtc gaaactgcct tcgttatcga catctgatca cgcttctgtg      60
gttgcgttga atctctttgt tgcacttctt tgtgcttgta ttgttcttgg tcatcttttg     120
gaagagaata gatggatgaa cgaatccatc accgccttgt tgattgggct aggcactggt     180
gttaccattt tgttgattag taaaggaaaa agctcgcatc ttctcgtctt tagtgaagat     240
```

```
ctttcttca tatatctttt gccacccatt atattcaatg cagggtttca agtaaaaaag    300
aagcagtttt tccgcaattt cgtgactatt atgcttttg gtgctgttgg gactattatt    360
tcttgcacaa tcatatctct aggtgtaaca cagttcttta agaagttgga cattggaacc   420
tttgacttgg gtgattatct tgctattggt gccatatttg ctgcaacaga ttcagtatgt   480
acactgcagg ttctgaatca agacgagaca cctttgcttt acagtcttgt attcggagag   540
ggtgttgtga atgatgcaac gtcagttgtg gtcttcaacg cgattcagag ctttgatctc   600
actcacctaa accacgaagc tgcttttcat cttcttggaa acttcttgta tttgtttctc   660
ctaagtacct tgcttggtgc tgcaaccggt ctgataagtg cgtatgttat caagaagcta   720
tactttggaa ggcactcaac tgaccgagag gttgcccctta tgatgctat ggcgtatctt    780 tcttatatgc ttgctgagct tttcgacttg agcggtatcc tcactgtgtt tttctgtggt   840
attgtgatgt cccattacac atggcacaat gtaacggaga gctcaagaat aacaacaaag   900 cataccttg caactttgtc atttcttgcg gagacattta ttttcttgta tgttggaatg    960
gatgccttgg acattgacaa gtggagatcc gtgagtgaca caccgggaac atcgatcgca   1020
gtgagctcaa tcctaatggg tctggtcatg gttggaagag cagcgttcgt cttccgttta   1080
tcgtttctat ctaacttagc caagaagaat caaagcgaga aaatcaactt taacatgcag   1140
gttgtgattt ggtggtctgg tctcatgaga ggtgctgtat ctatggctct tgcatacaac   1200
aagtttacaa gggccgggca cacagatgta cgcgggaatg caatcatgat cacgagtacg   1260
ataactgtct gtcttttag cacagtggtg tttggtatgc tgaccaaacc actcataagc    1320
tacctattac cgcaccagaa cgccaccacg agcatgttat ctgatgacaa cacccccaaaa   1380 tccatacata tcccttttgtt ggaccaagac tcgttcattg agccttcagg gaaccacaat   1440
gtgcctcggc ctgacagtat acgtggcttc ttg                                1473
```

<210> SEQ ID NO 8
<211> LENGTH: 491
<212> TYPE: PRT
<213> ORGANISM: Artificial
<220> FEATURE:
<223> OTHER INFORMATION: Putative amino acid encoded by modified AtNHX1 DL-2.

<400> SEQUENCE: 8

```
Met Leu Asp Ser Leu Val Ser Lys Leu Pro Ser Leu Ser Thr Ser Asp
1               5                   10                  15

His Ala Ser Val Val Ala Leu Asn Leu Phe Val Ala Leu Leu Cys Ala
                20                  25                  30

Cys Ile Val Leu Gly His Leu Leu Glu Glu Asn Arg Trp Met Asn Glu
            35                  40                  45

Ser Ile Thr Ala Leu Leu Ile Gly Leu Gly Thr Gly Val Thr Ile Leu
        50                  55                  60

Leu Ile Ser Lys Gly Lys Ser Ser His Leu Leu Val Phe Ser Glu Asp
65                  70                  75                  80

Leu Phe Phe Ile Tyr Leu Leu Pro Pro Ile Ile Phe Asn Ala Gly Phe
                85                  90                  95

Gln Val Lys Lys Lys Gln Phe Phe Arg Asn Phe Val Thr Ile Met Leu
            100                 105                 110

Phe Gly Ala Val Gly Thr Ile Ile Ser Cys Thr Ile Ile Ser Leu Gly
        115                 120                 125

Val Thr Gln Phe Phe Lys Lys Leu Asp Ile Gly Thr Phe Asp Leu Gly
```

```
                130                 135                 140
Asp Tyr Leu Ala Ile Gly Ala Ile Phe Ala Ala Thr Asp Ser Val Cys
145                 150                 155                 160

Thr Leu Gln Val Leu Asn Gln Asp Glu Thr Pro Leu Leu Tyr Ser Leu
                165                 170                 175

Val Phe Gly Glu Gly Val Val Asn Asp Ala Thr Ser Val Val Val Phe
            180                 185                 190

Asn Ala Ile Gln Ser Phe Asp Leu Thr His Leu Asn His Glu Ala Ala
        195                 200                 205

Phe His Leu Leu Gly Asn Phe Leu Tyr Leu Phe Leu Leu Ser Thr Leu
210                 215                 220

Leu Gly Ala Ala Thr Gly Leu Ile Ser Ala Tyr Val Ile Lys Lys Leu
225                 230                 235                 240

Tyr Phe Gly Arg His Ser Thr Asp Arg Glu Val Ala Leu Met Met Leu
                245                 250                 255

Met Ala Tyr Leu Ser Tyr Met Leu Ala Glu Leu Phe Asp Leu Ser Gly
            260                 265                 270

Ile Leu Thr Val Phe Phe Cys Gly Ile Val Met Ser His Tyr Thr Trp
        275                 280                 285

His Asn Val Thr Glu Ser Ser Arg Ile Thr Thr Lys His Thr Phe Ala
290                 295                 300

Thr Leu Ser Phe Leu Ala Glu Thr Phe Ile Phe Leu Tyr Val Gly Met
305                 310                 315                 320

Asp Ala Leu Asp Ile Asp Lys Trp Arg Ser Val Ser Asp Thr Pro Gly
                325                 330                 335

Thr Ser Ile Ala Val Ser Ser Ile Leu Met Gly Leu Val Met Val Gly
            340                 345                 350

Arg Ala Ala Phe Val Phe Pro Leu Ser Phe Leu Ser Asn Leu Ala Lys
        355                 360                 365

Lys Asn Gln Ser Glu Lys Ile Asn Phe Asn Met Gln Val Val Ile Trp
370                 375                 380

Trp Ser Gly Leu Met Arg Gly Ala Val Ser Met Ala Leu Ala Tyr Asn
385                 390                 395                 400

Lys Phe Thr Arg Ala Gly His Thr Asp Val Arg Gly Asn Ala Ile Met
                405                 410                 415

Ile Thr Ser Thr Ile Thr Val Cys Leu Phe Ser Thr Val Val Phe Gly
            420                 425                 430

Met Leu Thr Lys Pro Leu Ile Ser Tyr Leu Leu Pro His Gln Asn Ala
        435                 440                 445

Thr Thr Ser Met Leu Ser Asp Asp Asn Thr Pro Lys Ser Ile His Ile
450                 455                 460

Pro Leu Leu Asp Gln Asp Ser Phe Ile Glu Pro Ser Gly Asn His Asn
465                 470                 475                 480

Val Pro Arg Pro Asp Ser Ile Arg Gly Phe Leu
                485                 490

<210> SEQ ID NO 9
<211> LENGTH: 1362
<212> TYPE: DNA
<213> ORGANISM: Artificial
<220> FEATURE:
<223> OTHER INFORMATION: Modified AtNHX1 DL-3.

<400> SEQUENCE: 9
atgttggatt ctctagtgtc gaaactgcct tcgttatcga catctgatca cgcttctgtg      60
```

```
gttgcgttga atctctttgt tgcacttctt tgtgcttgta ttgttcttgg tcatcttttg      120
gaagagaata gatggatgaa cgaatccatc accgccttgt tgattgggct aggcactggt      180
gttaccattt tgttgattag taaaggaaaa agctcgcatc ttctcgtctt tagtgaagat      240
cttttcttca tatatctttt gccacccatt atattcaatg cagggtttca agtaaaaaag      300
aagcagtttt tccgcaattt cgtgactatt atgcttttg gtgctgttgg gactattatt       360
tcttgcacaa tcatatctct aggtgtaaca cagttcttta agaagttgga cattggaacc      420
tttgacttgg gtgattatct tgctattggt gccatatttg ctgcaacaga ttcagtatgt      480
acactgcagg ttctgaatca agacgagaca cctttgcttt acagtcttgt attcggagag      540
ggtgttgtga atgatgcaac gtcagttgtg gtcttcaacg cgattcagag ctttgatctc      600
actcacctaa accacgaagc tgcttttcat cttcttggaa acttcttgta tttgtttctc      660
ctaagtacct tgcttggtgc tgcaaccggt ctgataagtg cgtatgttat caagaagcta      720
tactttggaa ggcactcaac tgaccgagag gttgccctta tgatgcttat ggcgtatctt      780
tcttatatgc ttgctgagct tttcgacttg agcggtatcc tcactgtgtt tttctgtggt      840
attgtgatgt cccattacac atggcacaat gtaacggaga gctcaagaat aacaacaaag      900
catacctttg caactttgtc atttcttgcg gagacattta ttttcttgta tgttggaatg      960
gatgccttgg acattgacaa gtggagatcc gtgagtgaca caccgggaac atcgatcgca     1020
gtgagctcaa tcctaatggg tctggtcatg gttggaagag cagcgttcgt ctttccgtta     1080
tcgtttctat ctaacttagc caagaagaat caaagcgaga aaatcaactt taacatgcag     1140
gttgtgattt ggtggtctgg tctcatgaga ggtgctgtat ctatggctct tgcatacaac     1200
aagtttacaa gggccgggca cacagatgta cgcgggaatg caatcatgat cacgagtacg     1260
ataactgtct gtcttttag cacagtggtg tttggtatgc tgaccaaacc actcataagc     1320
tacctattac cgcaccagaa cgccaccacg agcatgttat ct                        1362
```

<210> SEQ ID NO 10
<211> LENGTH: 454
<212> TYPE: PRT
<213> ORGANISM: Artificial
<220> FEATURE:
<223> OTHER INFORMATION: Putative amino acid encoded by modified AtNHX1 DL-3.

<400> SEQUENCE: 10

```
Met Leu Asp Ser Leu Val Ser Lys Leu Pro Ser Leu Ser Thr Ser Asp
1               5                   10                  15

His Ala Ser Val Val Ala Leu Asn Leu Phe Val Ala Leu Leu Cys Ala
                20                  25                  30

Cys Ile Val Leu Gly His Leu Leu Glu Glu Asn Arg Trp Met Asn Glu
            35                  40                  45

Ser Ile Thr Ala Leu Leu Ile Gly Leu Gly Thr Gly Val Thr Ile Leu
        50                  55                  60

Leu Ile Ser Lys Gly Lys Ser Ser His Leu Leu Val Phe Ser Glu Asp
65                  70                  75                  80

Leu Phe Phe Ile Tyr Leu Leu Pro Pro Ile Ile Phe Asn Ala Gly Phe
                85                  90                  95

Gln Val Lys Lys Lys Gln Phe Phe Arg Asn Phe Val Thr Ile Met Leu
            100                 105                 110

Phe Gly Ala Val Gly Thr Ile Ile Ser Cys Thr Ile Ile Ser Leu Gly
        115                 120                 125
```

Val Thr Gln Phe Phe Lys Lys Leu Asp Ile Gly Thr Phe Asp Leu Gly
        130                 135                 140

Asp Tyr Leu Ala Ile Gly Ala Ile Phe Ala Ala Thr Asp Ser Val Cys
145                 150                 155                 160

Thr Leu Gln Val Leu Asn Gln Asp Glu Thr Pro Leu Leu Tyr Ser Leu
                165                 170                 175

Val Phe Gly Glu Gly Val Val Asn Asp Ala Thr Ser Val Val Phe
            180                 185                 190

Asn Ala Ile Gln Ser Phe Asp Leu Thr His Leu Asn His Glu Ala Ala
                195                 200                 205

Phe His Leu Leu Gly Asn Phe Leu Tyr Leu Phe Leu Leu Ser Thr Leu
        210                 215                 220

Leu Gly Ala Ala Thr Gly Leu Ile Ser Ala Tyr Val Ile Lys Lys Leu
225                 230                 235                 240

Tyr Phe Gly Arg His Ser Thr Asp Arg Glu Val Ala Leu Met Met Leu
                245                 250                 255

Met Ala Tyr Leu Ser Tyr Met Leu Ala Glu Leu Phe Asp Leu Ser Gly
            260                 265                 270

Ile Leu Thr Val Phe Phe Cys Gly Ile Val Met Ser His Tyr Thr Trp
        275                 280                 285

His Asn Val Thr Glu Ser Ser Arg Ile Thr Thr Lys His Thr Phe Ala
        290                 295                 300

Thr Leu Ser Phe Leu Ala Glu Thr Phe Ile Phe Leu Tyr Val Gly Met
305                 310                 315                 320

Asp Ala Leu Asp Ile Asp Lys Trp Arg Ser Val Ser Asp Thr Pro Gly
                325                 330                 335

Thr Ser Ile Ala Val Ser Ser Ile Leu Met Gly Leu Val Met Val Gly
            340                 345                 350

Arg Ala Ala Phe Val Phe Pro Leu Ser Phe Leu Ser Asn Leu Ala Lys
        355                 360                 365

Lys Asn Gln Ser Glu Lys Ile Asn Phe Asn Met Gln Val Val Ile Trp
370                 375                 380

Trp Ser Gly Leu Met Arg Gly Ala Val Ser Met Ala Leu Ala Tyr Asn
385                 390                 395                 400

Lys Phe Thr Arg Ala Gly His Thr Asp Val Arg Gly Asn Ala Ile Met
                405                 410                 415

Ile Thr Ser Thr Ile Thr Val Cys Leu Phe Ser Thr Val Phe Gly
            420                 425                 430

Met Leu Thr Lys Pro Leu Ile Ser Tyr Leu Leu Pro His Gln Asn Ala
        435                 440                 445

Thr Thr Ser Met Leu Ser
        450

<210> SEQ ID NO 11
<211> LENGTH: 1566
<212> TYPE: DNA
<213> ORGANISM: Artificial
<220> FEATURE:
<223> OTHER INFORMATION: Modified AtNHX1 NDL-1 cDNA.

<400> SEQUENCE: 11
atggcttctg tggttgcgtt gaatctcttt gttgcacttc tttgtgcttg tattgttctt        60
ggtcatcttt tggaagagaa tagatggatg aacgaatcca tcaccgcctt gttgattggg       120
ctaggcactg gtgttaccat tttgttgatt agtaaaggaa aaagctcgca tcttctcgtc       180

-continued

```
tttagtgaag atcttttctt catatatctt ttgccaccca ttatattcaa tgcagggttt    240
caagtaaaaa agaagcagtt tttccgcaat ttcgtgacta ttatgctttt tggtgctgtt    300
gggactatta tttcttgcac aatcatatct ctaggtgtaa cacagttctt taagaagttg    360
gacattggaa cctttgactt gggtgattat cttgctattg gtgccatatt gctgcaaca    420 gattcagtat gtacactgca ggttctgaat caagacgaga cacctttgct ttacagtctt    480
gtattcggag agggtgttgt gaatgatgca acgtcagttg tggtcttcaa cgcgattcag    540
agctttgatc tcactcacct aaaccacgaa gctgcttttc atcttcttgg aaacttcttg    600
tatttgtttc tcctaagtac cttgcttggt gctgcaaccg gtctgataag tgcgtatgtt    660
atcaagaagc tatactttgg aaggcactca actgaccgag aggttgccct tatgatgctt    720
atggcgtatc tttcttatat gcttgctgag cttttcgact tgagcggtat cctcactgtg    780
tttttctgtg gtattgtgat gtcccattac acatggcaca atgtaacgga gagctcaaga    840
ataacaacaa agcatacctt tgcaactttg tcatttcttg cggagacatt tatttttcttg   900 tatgttggaa tggatgcctt ggacattgac aagtggagat ccgtgagtga cacaccggga    960
acatcgatcg cagtgagctc aatcctaatg ggtctggtca tggttggaag agcagcgttc   1020
gtctttccgt tatcgtttct atctaactta gccaagaaga atcaaagcga gaaaatcaac   1080
tttaacatgc aggttgtgat ttggtggtct ggtctcatga gaggtgctgt atctatggct   1140
cttgcataca acaagtttac aagggccggg cacacagatg tacgcgggaa tgcaatcatg   1200
atcacgagta cgataactgt ctgtcttttt agcacagtgg tgtttggtat gctgaccaaa   1260
ccactcataa gctacctatt accgcaccag aacgccacca cgagcatgtt atctgatgac   1320
aacaccccaa aatccataca tatcccttg ttggaccaag actcgttcat tgagccttca    1380
gggaaccaca atgtgcctcg gcctgacagt atacgtggct tcttgacacg gcccactcga   1440
accgtgcatt actactggag acaatttgat gactccttca tgcgaccgt ctttggaggt    1500 cgtggctttg tacccttttgt tccaggttct ccaactgaga gaaaccctcc tgatcttagt   1560
aaggct                                                             1566
```

<210> SEQ ID NO 12
<211> LENGTH: 522
<212> TYPE: PRT
<213> ORGANISM: Artificial
<220> FEATURE:
<223> OTHER INFORMATION: Putative amino acid encoded by modified AtNHX1 NDL-1 cDNA.

<400> SEQUENCE: 12

```
Met Ala Ser Val Val Ala Leu Asn Leu Phe Val Ala Leu Leu Cys Ala
1               5                   10                  15

Cys Ile Val Leu Gly His Leu Leu Glu Glu Asn Arg Trp Met Asn Glu
            20                  25                  30

Ser Ile Thr Ala Leu Leu Ile Gly Leu Gly Thr Gly Val Thr Ile Leu
        35                  40                  45

Leu Ile Ser Lys Gly Lys Ser Ser His Leu Leu Val Phe Ser Glu Asp
    50                  55                  60

Leu Phe Phe Ile Tyr Leu Leu Pro Pro Ile Ile Phe Asn Ala Gly Phe
65                  70                  75                  80

Gln Val Lys Lys Lys Gln Phe Phe Arg Asn Phe Val Thr Ile Met Leu
                85                  90                  95

Phe Gly Ala Val Gly Thr Ile Ile Ser Cys Thr Ile Ile Ser Leu Gly
```

```
                100             105             110
Val Thr Gln Phe Phe Lys Lys Leu Asp Ile Gly Thr Phe Asp Leu Gly
        115                 120                 125

Asp Tyr Leu Ala Ile Gly Ala Ile Phe Ala Ala Thr Asp Ser Val Cys
    130                 135                 140

Thr Leu Gln Val Leu Asn Gln Asp Glu Thr Pro Leu Leu Tyr Ser Leu
145                 150                 155                 160

Val Phe Gly Glu Gly Val Val Asn Asp Ala Thr Ser Val Val Val Phe
                165                 170                 175

Asn Ala Ile Gln Ser Phe Asp Leu Thr His Leu Asn His Glu Ala Ala
            180                 185                 190

Phe His Leu Leu Gly Asn Phe Leu Tyr Leu Phe Leu Leu Ser Thr Leu
        195                 200                 205

Leu Gly Ala Ala Thr Gly Leu Ile Ser Ala Tyr Val Ile Lys Lys Leu
    210                 215                 220

Tyr Phe Gly Arg His Ser Thr Asp Arg Glu Val Ala Leu Met Met Leu
225                 230                 235                 240

Met Ala Tyr Leu Ser Tyr Met Leu Ala Glu Leu Phe Asp Leu Ser Gly
                245                 250                 255

Ile Leu Thr Val Phe Phe Cys Gly Ile Val Met Ser His Tyr Thr Trp
            260                 265                 270

His Asn Val Thr Glu Ser Ser Arg Ile Thr Thr Lys His Thr Phe Ala
        275                 280                 285

Thr Leu Ser Phe Leu Ala Glu Thr Phe Ile Phe Leu Tyr Val Gly Met
    290                 295                 300

Asp Ala Leu Asp Ile Asp Lys Trp Arg Ser Val Ser Asp Thr Pro Gly
305                 310                 315                 320

Thr Ser Ile Ala Val Ser Ser Ile Leu Met Gly Leu Val Met Val Gly
                325                 330                 335

Arg Ala Ala Phe Val Phe Pro Leu Ser Phe Leu Ser Asn Leu Ala Lys
            340                 345                 350

Lys Asn Gln Ser Glu Lys Ile Asn Phe Asn Met Gln Val Val Ile Trp
        355                 360                 365

Trp Ser Gly Leu Met Arg Gly Ala Val Ser Met Ala Leu Ala Tyr Asn
    370                 375                 380

Lys Phe Thr Arg Ala Gly His Thr Asp Val Arg Gly Asn Ala Ile Met
385                 390                 395                 400

Ile Thr Ser Thr Ile Thr Val Cys Leu Phe Ser Thr Val Val Phe Gly
                405                 410                 415

Met Leu Thr Lys Pro Leu Ile Ser Tyr Leu Leu Pro His Gln Asn Ala
            420                 425                 430

Thr Thr Ser Met Leu Ser Asp Asp Asn Thr Pro Lys Ser Ile His Ile
        435                 440                 445

Pro Leu Leu Asp Gln Asp Ser Phe Ile Glu Pro Ser Gly Asn His Asn
    450                 455                 460

Val Pro Arg Pro Asp Ser Ile Arg Gly Phe Leu Thr Arg Pro Thr Arg
465                 470                 475                 480

Thr Val His Tyr Tyr Trp Arg Gln Phe Asp Asp Ser Phe Met Arg Pro
                485                 490                 495

Val Phe Gly Gly Arg Gly Phe Val Pro Phe Val Pro Gly Ser Pro Thr
            500                 505                 510

Glu Arg Asn Pro Pro Asp Leu Ser Lys Ala
        515                 520
```

-continued

<210> SEQ ID NO 13
<211> LENGTH: 1410
<212> TYPE: DNA
<213> ORGANISM: Artificial
<220> FEATURE:
<223> OTHER INFORMATION: NDL-2 cDNA.

<400> SEQUENCE: 13

| | | | | | |
|---|---|---|---|---|---|
| atgaaaagct | cgcatcttct | cgtctttagt | gaagatcttt | tcttcatata | tcttttgcca | 60 |
| cccattatat | tcaatgcagg | gtttcaagta | aaaagaagc | agttttccg | caatttcgtg | 120 |
| actattatgc | tttttggtgc | tgttgggact | attatttctt | gcacaatcat | atctctaggt | 180 |
| gtaacacagt | tctttaagaa | gttggacatt | ggaaccttg | acttgggtga | ttatcttgct | 240 |
| attggtgcca | tatttgctgc | aacagattca | gtatgtacac | tgcaggttct | gaatcaagac | 300 |
| gagacacctt | tgctttacag | tcttgtattc | ggagagggtg | ttgtgaatga | tgcaacgtca | 360 |
| gttgtggtct | tcaacgcgat | tcagagcttt | gatctcactc | acctaaacca | cgaagctgct | 420 |
| tttcatcttc | ttggaaactt | cttgtatttg | tttctcctaa | gtaccttgct | tggtgctgca | 480 |
| accggtctga | taagtgcgta | tgttatcaag | aagctatact | ttggaaggca | ctcaactgac | 540 |
| cgagaggttg | cccttatgat | gcttatggcg | tatcttctt | atatgcttgc | tgagcttttc | 600 |
| gacttgagcg | gtatcctcac | tgtgttttc | tgtggtattg | tgatgtccca | ttacacatgg | 660 |
| cacaatgtaa | cggagagctc | aagaataaca | acaaagcata | cctttgcaac | tttgtcattt | 720 |
| cttgcggaga | catttatttt | cttgtatgtt | ggaatggatg | ccttggacat | tgacaagtgg | 780 |
| agatccgtga | gtgacacacc | gggaacatcg | atcgcagtga | gctcaatcct | aatgggtctg | 840 |
| gtcatggttg | gaagagcagc | gttcgtcttt | ccgttatcgt | ttctatctaa | cttagccaag | 900 |
| aagaatcaaa | gcgagaaaat | caactttaac | atgcaggttg | tgatttggtg | gtctggtctc | 960 |
| atgagaggtg | ctgtatctat | ggctcttgca | tacaacaagt | ttacaagggc | cgggcacaca | 1020 |
| gatgtacgcg | ggaatgcaat | catgatcacg | agtacgataa | ctgtctgtct | ttttagcaca | 1080 |
| gtggtgtttg | gtatgctgac | caaaccactc | ataagctacc | tattaccgca | ccagaacgcc | 1140 |
| accacgagca | tgttatctga | tgacaacacc | ccaaaatcca | tacatatccc | tttgttggac | 1200 |
| caagactcgt | tcattgagcc | ttcagggaac | acaatgtgc | ctcggcctga | cagtatacgt | 1260 |
| ggcttcttga | cacggcccac | tcgaaccgtg | cattactact | ggagacaatt | tgatgactcc | 1320 |
| ttcatgcgac | ccgtctttgg | aggtcgtggc | tttgtaccct | tgttccagg | ttctccaact | 1380 |
| gagagaaacc | ctcctgatct | tagtaaggct | | | | 1410 |

<210> SEQ ID NO 14
<211> LENGTH: 470
<212> TYPE: PRT
<213> ORGANISM: Artificial
<220> FEATURE:
<223> OTHER INFORMATION: Putative amino acid encoded by modified AtNHX1
    NDL-2 cDNA.

<400> SEQUENCE: 14

Met Lys Ser Ser His Leu Leu Val Phe Ser Glu Asp Leu Phe Phe Ile
1               5                   10                  15

Tyr Leu Leu Pro Pro Ile Ile Phe Asn Ala Gly Phe Gln Val Lys Lys
            20                  25                  30

Lys Gln Phe Phe Arg Asn Phe Val Thr Ile Met Leu Phe Gly Ala Val
        35                  40                  45

```
Gly Thr Ile Ile Ser Cys Thr Ile Ile Ser Leu Gly Val Thr Gln Phe
     50                  55                  60

Phe Lys Lys Leu Asp Ile Gly Thr Phe Asp Leu Gly Asp Tyr Leu Ala
 65                  70                  75                  80

Ile Gly Ala Ile Phe Ala Ala Thr Asp Ser Val Cys Thr Leu Gln Val
                     85                  90                  95

Leu Asn Gln Asp Glu Thr Pro Leu Leu Tyr Ser Leu Val Phe Gly Glu
                100                 105                 110

Gly Val Val Asn Asp Ala Thr Ser Val Val Phe Asn Ala Ile Gln
                115                 120                 125

Ser Phe Asp Leu Thr His Leu Asn His Glu Ala Ala Phe His Leu Leu
    130                 135                 140

Gly Asn Phe Leu Tyr Leu Phe Leu Leu Ser Thr Leu Leu Gly Ala Ala
145                 150                 155                 160

Thr Gly Leu Ile Ser Ala Tyr Val Ile Lys Lys Leu Tyr Phe Gly Arg
                165                 170                 175

His Ser Thr Asp Arg Glu Val Ala Leu Met Met Leu Met Ala Tyr Leu
                180                 185                 190

Ser Tyr Met Leu Ala Glu Leu Phe Asp Leu Ser Gly Ile Leu Thr Val
    195                 200                 205

Phe Phe Cys Gly Ile Val Met Ser His Tyr Thr Trp His Asn Val Thr
210                 215                 220

Glu Ser Ser Arg Ile Thr Thr Lys His Thr Phe Ala Thr Leu Ser Phe
225                 230                 235                 240

Leu Ala Glu Thr Phe Ile Phe Leu Tyr Val Gly Met Asp Ala Leu Asp
                245                 250                 255

Ile Asp Lys Trp Arg Ser Val Ser Asp Thr Pro Gly Thr Ser Ile Ala
                260                 265                 270

Val Ser Ser Ile Leu Met Gly Leu Val Met Val Gly Arg Ala Ala Phe
    275                 280                 285

Val Phe Pro Leu Ser Phe Leu Ser Asn Leu Ala Lys Lys Asn Gln Ser
    290                 295                 300

Glu Lys Ile Asn Phe Asn Met Gln Val Val Ile Trp Trp Ser Gly Leu
305                 310                 315                 320

Met Arg Gly Ala Val Ser Met Ala Leu Ala Tyr Asn Lys Phe Thr Arg
                325                 330                 335

Ala Gly His Thr Asp Val Arg Gly Asn Ala Ile Met Ile Thr Ser Thr
                340                 345                 350

Ile Thr Val Cys Leu Phe Ser Thr Val Val Phe Gly Met Leu Thr Lys
        355                 360                 365

Pro Leu Ile Ser Tyr Leu Leu Pro His Gln Asn Ala Thr Thr Ser Met
    370                 375                 380

Leu Ser Asp Asp Asn Thr Pro Lys Ser Ile His Ile Pro Leu Leu Asp
385                 390                 395                 400

Gln Asp Ser Phe Ile Glu Pro Ser Gly Asn His Asn Val Pro Arg Pro
                405                 410                 415

Asp Ser Ile Arg Gly Phe Leu Thr Arg Pro Thr Arg Thr Val His Tyr
                420                 425                 430

Tyr Trp Arg Gln Phe Asp Asp Ser Phe Met Arg Pro Val Phe Gly Gly
                435                 440                 445

Arg Gly Phe Val Pro Phe Val Pro Gly Ser Pro Thr Glu Arg Asn Pro
450                 455                 460

Pro Asp Leu Ser Lys Ala
```

-continued

<210> SEQ ID NO 15
<211> LENGTH: 1323
<212> TYPE: DNA
<213> ORGANISM: Artificial
<220> FEATURE:
<223> OTHER INFORMATION: NDL-3 cDNA.

<400> SEQUENCE: 15

```
atgaaaaaga agcagttttt ccgcaatttc gtgactatta tgcttttgg tgctgttggg      60
actattattt cttgcacaat catatctcta ggtgtaacac agttctttaa gaagttggac    120
attggaacct tgacttgggt gattatctt gctattggtg ccatatttgc tgcaacagat    180
tcagtatgta cactgcaggt tctgaatcaa gacgagacac ctttgcttta cagtcttgta    240
ttcggagagg gtgttgtgaa tgatgcaacg tcagttgtgg tcttcaacgc gattcagagc    300
tttgatctca ctcacctaaa ccacgaagct gcttttcatc ttcttggaaa cttcttgtat    360
tgtttctcc taagtacctt gcttggtgct gcaaccggtc tgataagtgc gtatgttatc    420
aagaagctat actttggaag cactcaact gaccgagagg ttgcccttat gatgcttatg    480
gcgtatcttt cttatatgct tgctgagctt ttcgacttga gcggtatcct cactgtgttt    540
ttctgtggta ttgtgatgtc ccattacaca tggcacaatg taacggagag ctcaagaata    600
acaacaaagc ataccttgc aactttgtca tttcttgcgg agacatttat tttcttgtat    660
gttggaatgg atgccttgga cattgacaag tggagatccg tgagtgacac accgggaaca    720
tcgatcgcag tgagctcaat cctaatgggt ctggtcatgg ttggaagagc agcgttcgtc    780
tttccgttat cgtttctatc taacttagcc aagaagaatc aaagcgagaa atcaacttt    840
aacatgcagg ttgtgatttg gtggtctggt ctcatgagag gtgctgtatc tatggctctt    900
gcatacaaca agtttacaag gccgggcac acagatgtac gcgggaatgc aatcatgatc    960
acgagtacga taactgtctg tctttttagc acagtggtgt ttggtatgct gaccaaacca   1020
ctcataagct acctattacc gcaccagaac gccaccacga gcatgttatc tgatgacaac   1080
accccaaaat ccatacatat cccttttgttg gaccaagact cgttcattga gccttcaggg   1140
aaccacaatg tgcctcggcc tgacagtata cgtggcttct tgacacggcc cactcgaacc   1200
gtgcattact actggagaca atttgatgac tccttcatgc gacccgtctt tggaggtcgt   1260
ggctttgtac cctttgttcc aggttctcca actgagagaa accctcctga tcttagtaag   1320
gct                                                                  1323
```

<210> SEQ ID NO 16
<211> LENGTH: 439
<212> TYPE: PRT
<213> ORGANISM: Artificial
<220> FEATURE:
<223> OTHER INFORMATION: Putative amino acid encodied by modified AtNHX1
      NDL-3 cDNA.

<400> SEQUENCE: 16

```
Met Lys Lys Lys Gln Phe Phe Arg Asn Phe Val Thr Ile Met Leu Phe
1               5                   10                  15

Gly Ala Val Gly Thr Ile Ile Ser Cys Thr Ile Ile Ser Leu Gly Val
            20                  25                  30

Thr Gln Phe Phe Lys Lys Leu Asp Ile Gly Thr Phe Asp Leu Gly Asp
        35                  40                  45

Tyr Leu Ala Ile Gly Ala Ile Phe Ala Ala Thr Asp Ser Val Cys Thr
```

```
                50                  55                  60
Leu Gln Val Leu Asn Gln Asp Glu Thr Pro Leu Leu Tyr Ser Leu Val
 65                  70                  75                  80

Phe Gly Glu Gly Val Val Asn Asp Ala Thr Ser Trp Val Phe Asn Ala
                 85                  90                  95

Ile Gln Ser Phe Asp Leu Thr His Leu Asn His Glu Ala Ala Phe His
            100                 105                 110

Leu Leu Gly Asn Phe Leu Tyr Leu Phe Leu Leu Ser Thr Leu Leu Gly
        115                 120                 125

Ala Ala Thr Gly Leu Ile Ser Ala Tyr Val Ile Lys Lys Leu Tyr Phe
    130                 135                 140

Gly Arg His Ser Thr Asp Arg Glu Val Ala Leu Met Met Leu Met Ala
145                 150                 155                 160

Tyr Leu Ser Tyr Met Leu Ala Glu Leu Phe Asp Leu Ser Gly Ile Leu
                165                 170                 175

Thr Val Phe Phe Cys Gly Ile Val Met Ser His Tyr Thr Trp His Asn
            180                 185                 190

Val Thr Glu Ser Ser Arg Ile Thr Thr Lys His Thr Phe Ala Thr Leu
        195                 200                 205

Ser Phe Leu Ala Glu Thr Phe Ile Phe Leu Tyr Val Gly Met Asp Ala
    210                 215                 220

Leu Asp Ile Asp Lys Trp Arg Ser Val Ser Asp Thr Pro Gly Thr Ser
225                 230                 235                 240

Ile Ala Val Ser Ser Ile Leu Met Gly Leu Val Met Val Gly Arg Ala
                245                 250                 255

Ala Phe Val Phe Pro Leu Ser Phe Leu Ser Asn Leu Ala Lys Lys Asn
            260                 265                 270

Gln Ser Glu Lys Ile Asn Phe Asn Met Gln Trp Ile Trp Trp Ser Gly
        275                 280                 285

Leu Met Arg Gly Ala Val Ser Met Ala Leu Ala Tyr Asn Lys Phe Thr
    290                 295                 300

Arg Ala Gly His Thr Asp Val Arg Gly Asn Ala Ile Met Ile Thr Ser
305                 310                 315                 320

Thr Ile Thr Val Cys Leu Phe Ser Thr Val Val Phe Gly Met Leu Thr
                325                 330                 335

Lys Pro Leu Ile Ser Tyr Leu Leu Pro His Gln Asn Ala Thr Thr Ser
            340                 345                 350

Met Leu Ser Asp Asp Asn Thr Pro Lys Ser Ile His Ile Pro Leu Leu
        355                 360                 365

Asp Gln Asp Ser Phe Ile Glu Pro Ser Gly Asn His Asn Val Pro Arg
    370                 375                 380

Pro Asp Ser Ile Arg Gly Phe Leu Thr Arg Pro Thr Arg Thr Val His
385                 390                 395                 400

Tyr Tyr Trp Arg Gln Phe Asp Asp Ser Phe Met Arg Pro Val Phe Gly
                405                 410                 415

Gly Arg Gly Phe Val Pro Phe Val Pro Gly Ser Pro Thr Glu Arg Asn
            420                 425                 430

Pro Pro Asp Leu Ser Lys Ala
        435

<210> SEQ ID NO 17
<211> LENGTH: 35
<212> TYPE: DNA
<213> ORGANISM: Artificial
```

```
<220> FEATURE:
<223> OTHER INFORMATION: Putative amino acid encodied by modified AtNHX1
      NDL-3 cDNA.

<400> SEQUENCE: 17
ggagacaatt tgatgactgc ttcatgcgac ccgtc                                35

<210> SEQ ID NO 18
<211> LENGTH: 35
<212> TYPE: DNA
<213> ORGANISM: Artificial
<220> FEATURE:
<223> OTHER INFORMATION: Primer SM-23-R

<400> SEQUENCE: 18
gacgggtcgc atgaagcagt catcaaattg tctcc                                35

<210> SEQ ID NO 19
<211> LENGTH: 38
<212> TYPE: DNA
<213> ORGANISM: Artificial
<220> FEATURE:
<223> OTHER INFORMATION: Primer EXCH-5

<400> SEQUENCE: 19
agctaggatc cggatctaga agaagataac aatgttgg                             38

<210> SEQ ID NO 20
<211> LENGTH: 33
<212> TYPE: DNA
<213> ORGANISM: Artificial
<220> FEATURE:
<223> OTHER INFORMATION: Primer EXCH-DL-1

<400> SEQUENCE: 20
agctgaattc ctagggtaca aagccacgac ctc                                  33

<210> SEQ ID NO 21
<211> LENGTH: 32
<212> TYPE: DNA
<213> ORGANISM: Artificial
<220> FEATURE:
<223> OTHER INFORMATION: Primer EXCH-DL-2

<400> SEQUENCE: 21
agctgaattc ctacaagaag ccacgtatac tg                                   32

<210> SEQ ID NO 22
<211> LENGTH: 32
<212> TYPE: DNA
<213> ORGANISM: Artificial
<220> FEATURE:
<223> OTHER INFORMATION: Primer EXCH-DL-3

<400> SEQUENCE: 22
agctgaattc ctaagataac atgctcgtgg tg                                   32
```